United States Patent
Goldberg et al.

(10) Patent No.: US 8,882,666 B1
(45) Date of Patent: Nov. 11, 2014

(54) PERSONAL HEALTH MONITORING AND/OR COMMUNICATION SYSTEM

(75) Inventors: Jason Goldberg, Toronto (CA); Thomas C. Beckerman, Toronto (CA)

(73) Assignee: Ideal Life Inc., Ontario (CA)

( * ) Notice: Subject to any disclaimer, the term of this patent is extended or adjusted under 35 U.S.C. 154(b) by 756 days.

(21) Appl. No.: 11/108,355

(22) Filed: Apr. 18, 2005

Related U.S. Application Data

(63) Continuation-in-part of application No. 10/868,676, filed on Jun. 15, 2004, now abandoned, which is a continuation of application No. 09/075,097, filed on May 8, 1998, now Pat. No. 6,254,565.

(60) Provisional application No. 60/562,876, filed on Apr. 16, 2004.

(51) Int. Cl.
*A61B 5/00* (2006.01)
*A61B 5/02* (2006.01)
*G06F 19/00* (2011.01)

(52) U.S. Cl.
CPC .......... *G06F 19/3418* (2013.01); *A61B 5/0002* (2013.01); *G06F 19/3406* (2013.01); *G06F 19/345* (2013.01); *G06F 19/3412* (2013.01); *G06F 19/3487* (2013.01); *G06F 19/3425* (2013.01); *A61B 2505/07* (2013.01); *A61B 5/02* (2013.01); *Y10S 128/92* (2013.01); *Y10S 128/903* (2013.01)
USPC ................... 600/301; 705/2; 705/3; 128/920; 128/903; 340/539.12; 709/217; 709/240

(58) Field of Classification Search
USPC ............................ 600/300–301; 128/903–905
See application file for complete search history.

(56) References Cited

U.S. PATENT DOCUMENTS

| | | | |
|---|---|---|---|
| 3,804,524 A | 4/1974 | Jocoy et al. |
| 4,394,773 A | 7/1983 | Ruell |
| 4,408,323 A | 10/1983 | Montgomery |
| 4,453,247 A | 6/1984 | Suzuki et al. |

(Continued)

FOREIGN PATENT DOCUMENTS

| | | |
|---|---|---|
| WO | WO 01/65810 A1 | 9/2001 |
| WO | WO 01/97703 A2 | 12/2001 |
| WO | WO0228123 A2 * | 4/2002 |

OTHER PUBLICATIONS

Techweb, "PDA" http://www.techweb.com/encyclopedia/printArticlePage.jhtml?term=PDA.*

(Continued)

*Primary Examiner* — William Thomson
*Assistant Examiner* — Marie Archer
(74) *Attorney, Agent, or Firm* — Frommer Lawrence & Haug LLP; Frank J. DeRosa

(57) ABSTRACT

Monitoring systems are provided for monitoring physiologic parameters of at least one subject. The systems generally include a monitoring device or a plurality of monitoring devices, and a transmission device associated with the one or the plurality of the monitoring devices. The monitoring device(s) includes at least one physiologic sensor for measuring at least one physiologic parameter of a subject and a wireless communication unit. The transmission device includes at least one communication unit for communicating with the monitoring device wirelessly and for communicating with a remote computer. The monitoring device(s) communicate data measured with the monitoring device to the transmission device wirelessly and the transmission device communicates the measured data to the remote computer.

20 Claims, 8 Drawing Sheets

(56) References Cited

U.S. PATENT DOCUMENTS

| | | | |
|---|---|---|---|
| 4,581,735 A | 4/1986 | Flamm et al. | |
| 4,731,726 A | 3/1988 | Allen, III | |
| 4,782,485 A | 11/1988 | Gollub | |
| 4,831,242 A | 5/1989 | Englehardt et al. | |
| 4,857,916 A | 8/1989 | Bellin | |
| 4,905,293 A | 2/1990 | Asai et al. | |
| 4,914,650 A | 4/1990 | Sriram | |
| 5,144,680 A | 9/1992 | Kobayashi et al. | |
| 5,213,555 A | 5/1993 | Hood et al. | |
| 5,307,263 A | 4/1994 | Brown | |
| 5,390,238 A | 2/1995 | Kirk et al. | |
| 5,412,463 A | 5/1995 | Sibbald et al. | |
| 5,420,936 A | 5/1995 | Fitzpatrick et al. | |
| 5,467,403 A | 11/1995 | Fishbine et al. | |
| 5,546,471 A | 8/1996 | Merjanian | |
| 5,576,952 A | 11/1996 | Stutman et al. | |
| 5,590,632 A | 1/1997 | Kato et al. | |
| 5,603,179 A | 2/1997 | Adams | |
| 5,617,423 A | 4/1997 | Li et al. | |
| 5,687,732 A * | 11/1997 | Inagaki et al. | 600/503 |
| 5,701,904 A | 12/1997 | Simmons et al. | |
| 5,704,366 A | 1/1998 | Tacklind et al. | |
| 5,713,350 A | 2/1998 | Yokota et al. | |
| 5,732,133 A | 3/1998 | Mark | |
| 5,772,586 A | 6/1998 | Heinonen et al. | |
| 5,796,858 A | 8/1998 | Zhou et al. | |
| 5,822,715 A | 10/1998 | Worthington et al. | |
| 5,827,180 A | 10/1998 | Goodman | |
| 5,828,773 A | 10/1998 | Setlak et al. | |
| 5,828,943 A | 10/1998 | Brown | |
| 5,832,448 A | 11/1998 | Brown | |
| 5,838,306 A | 11/1998 | O'Connor et al. | |
| 5,840,020 A | 11/1998 | Heinonen et al. | |
| 5,852,670 A | 12/1998 | Setlak et al. | |
| 5,862,803 A | 1/1999 | Besson et al. | |
| 5,872,834 A | 2/1999 | Teitelbaum | |
| 5,875,430 A | 2/1999 | Koether | |
| 5,879,163 A | 3/1999 | Brown et al. | |
| 5,897,493 A | 4/1999 | Brown | |
| 5,899,855 A | 5/1999 | Brown | |
| 5,902,234 A * | 5/1999 | Webb | 600/300 |
| 5,910,946 A | 6/1999 | Csapo | |
| 5,920,642 A | 7/1999 | Merjanian | |
| 5,926,261 A | 7/1999 | Hoshino | |
| 5,933,136 A | 8/1999 | Brown | |
| 5,940,801 A | 8/1999 | Brown | |
| 5,950,632 A | 9/1999 | Reber et al. | |
| 5,951,300 A | 9/1999 | Brown | |
| 5,953,322 A | 9/1999 | Kimball | |
| 5,956,501 A | 9/1999 | Brown | |
| 5,957,854 A | 9/1999 | Besson et al. | |
| 5,960,403 A | 9/1999 | Brown | |
| 5,970,458 A | 10/1999 | Petkovset | |
| 5,985,559 A | 11/1999 | Brown | |
| 5,991,408 A | 11/1999 | Pearson et al. | |
| 5,997,476 A | 12/1999 | Brown | |
| 6,011,860 A | 1/2000 | Fujieda et al. | |
| 6,016,476 A | 1/2000 | Maes et al. | |
| 6,024,699 A | 2/2000 | Surwit et al. | |
| 6,028,950 A | 2/2000 | Merjanian | |
| 6,032,119 A | 2/2000 | Brown et al. | |
| 6,047,203 A | 4/2000 | Sackner et al. | |
| 6,050,940 A | 4/2000 | Braun et al. | |
| 6,064,737 A | 5/2000 | Rhoads | |
| 6,072,396 A | 6/2000 | Gaukel | |
| 6,078,848 A | 6/2000 | Bernstein et al. | |
| 6,078,908 A | 6/2000 | Schmitz | |
| 6,088,585 A | 7/2000 | Schmitt et al. | |
| 6,101,478 A | 8/2000 | Brown | |
| 6,111,977 A | 8/2000 | Scott et al. | |
| 6,128,563 A | 10/2000 | Muraro | |
| 6,135,951 A | 10/2000 | Richardson et al. | |
| 6,141,436 A | 10/2000 | Srey et al. | |
| 6,144,837 A | 11/2000 | Quy | |
| 6,151,586 A | 11/2000 | Brown | |
| 6,154,727 A | 11/2000 | Karp et al. | |
| 6,160,903 A | 12/2000 | Hamid et al. | |
| 6,161,095 A | 12/2000 | Brown | |
| 6,167,362 A | 12/2000 | Brown et al. | |
| 6,168,563 B1 | 1/2001 | Brown | |
| 6,175,752 B1 | 1/2001 | Say et al. | |
| 6,175,922 B1 | 1/2001 | Wang | |
| 6,177,950 B1 | 1/2001 | Robb | |
| 6,191,410 B1 | 2/2001 | Johnson | |
| 6,196,970 B1 | 3/2001 | Brown | |
| 6,198,394 B1 * | 3/2001 | Jacobsen et al. | 340/573.1 |
| 6,219,793 B1 | 4/2001 | Li et al. | |
| 6,221,010 B1 | 4/2001 | Lucas | |
| 6,233,539 B1 | 5/2001 | Brown | |
| 6,240,393 B1 | 5/2001 | Brown | |
| 6,246,992 B1 | 6/2001 | Brown | |
| 6,248,065 B1 | 6/2001 | Brown | |
| 6,249,672 B1 | 6/2001 | Castiel | |
| 6,260,022 B1 | 7/2001 | Brown | |
| 6,260,065 B1 | 7/2001 | Leiba et al. | |
| 6,270,455 B1 | 8/2001 | Brown | |
| 6,282,304 B1 | 8/2001 | Novikov et al. | |
| 6,289,238 B1 | 9/2001 | Besson et al. | |
| 6,302,844 B1 | 10/2001 | Walker et al. | |
| 6,330,426 B2 | 12/2001 | Brown et al. | |
| 6,330,457 B1 | 12/2001 | Yoon | |
| 6,334,778 B1 | 1/2002 | Brown | |
| 6,336,900 B1 * | 1/2002 | Alleckson et al. | 600/485 |
| 6,337,918 B1 | 1/2002 | Holehan | |
| 6,337,919 B1 | 1/2002 | Dunton | |
| 6,366,871 B1 * | 4/2002 | Geva | 702/188 |
| 6,368,273 B1 | 4/2002 | Brown | |
| 6,375,469 B1 | 4/2002 | Brown | |
| 6,375,614 B1 | 4/2002 | Braun et al. | |
| 6,379,301 B1 | 4/2002 | Worthington et al. | |
| 6,381,577 B1 | 4/2002 | Brown | |
| 6,402,691 B1 | 6/2002 | Peddicord et al. | |
| 6,404,862 B1 | 6/2002 | Holt | |
| 6,440,069 B1 | 8/2002 | Raymond et al. | |
| 6,441,747 B1 | 8/2002 | Khair et al. | |
| 6,454,705 B1 | 9/2002 | Cosentino et al. | |
| 6,478,736 B1 * | 11/2002 | Mault | 600/300 |
| 6,493,437 B1 | 12/2002 | Olshansky | |
| 6,525,670 B1 * | 2/2003 | Doi et al. | 600/300 |
| 6,558,320 B1 * | 5/2003 | Causey et al. | 600/300 |
| 6,577,893 B1 | 6/2003 | Besson et al. | |
| 6,579,231 B1 | 6/2003 | Phipps | |
| 6,589,169 B1 | 7/2003 | Surwit et al. | |
| 6,594,523 B1 | 7/2003 | Levine | |
| 6,595,929 B2 * | 7/2003 | Stivoric et al. | 600/549 |
| 6,599,250 B2 | 7/2003 | Webb et al. | |
| 6,602,191 B2 | 8/2003 | Quy | |
| 6,611,705 B2 | 8/2003 | Hopman et al. | |
| 6,638,218 B2 | 10/2003 | Bulat | |
| 6,643,542 B1 | 11/2003 | Kawanishi | |
| 6,658,287 B1 | 12/2003 | Litt et al. | |
| 6,694,186 B2 | 2/2004 | Bardy | |
| 6,725,209 B1 | 4/2004 | Iliff | |
| 6,749,537 B1 | 6/2004 | Hickman | |
| 6,770,029 B2 | 8/2004 | Iliff | |
| 6,790,178 B1 * | 9/2004 | Mault et al. | 600/300 |
| 6,840,904 B2 | 1/2005 | Goldberg | |
| 6,968,375 B1 * | 11/2005 | Brown | 709/224 |
| 7,024,369 B1 | 4/2006 | Brown et al. | |
| 7,261,690 B2 | 8/2007 | Teller et al. | |
| 2001/0012201 A1 | 8/2001 | Fries et al. | |
| 2001/0048025 A1 | 12/2001 | Shinn | |
| 2001/0048359 A1 | 12/2001 | Yamane et al. | |
| 2001/0049785 A1 | 12/2001 | Kawan et al. | |
| 2001/0051924 A1 | 12/2001 | Uberti | |
| 2002/0003892 A1 | 1/2002 | Iwanaga | |
| 2002/0016719 A1 | 2/2002 | Nemeth et al. | |
| 2002/0022973 A1 | 2/2002 | Sun et al. | |
| 2002/0065682 A1 | 5/2002 | Goldenberg | |
| 2002/0082867 A1 * | 6/2002 | MacCarter et al. | 705/2 |
| 2002/0106077 A1 | 8/2002 | Moquin et al. | |
| 2002/0120200 A1 | 8/2002 | Brockway et al. | |
| 2002/0122415 A1 | 9/2002 | Chang et al. | |
| 2002/0128804 A1 * | 9/2002 | Geva | 702/188 |

(56) References Cited

U.S. PATENT DOCUMENTS

| | | | |
|---|---|---|---|
| 2002/0133377 A1 | 9/2002 | Brown | |
| 2002/0152391 A1 | 10/2002 | Willins et al. | |
| 2002/0174345 A1 | 11/2002 | Patel | |
| 2003/0046557 A1 | 3/2003 | Miller et al. | |
| 2003/0081752 A1 | 5/2003 | Trandal | |
| 2003/0126593 A1 | 7/2003 | Mault | |
| 2004/0019259 A1 | 1/2004 | Brown et al. | |
| 2004/0034286 A1 | 2/2004 | Kasper et al. | |
| 2004/0059599 A1 | 3/2004 | McIvor | |
| 2004/0102683 A1 | 5/2004 | Khanuja et al. | |
| 2004/0152957 A1 | 8/2004 | Stivoric et al. | |
| 2004/0152993 A1 | 8/2004 | Bardy | |
| 2004/0167580 A1 | 8/2004 | Mann et al. | |
| 2004/0230127 A1 | 11/2004 | Bardy | |
| 2005/0137481 A1 | 6/2005 | Sheard et al. | |
| 2005/0144042 A1 | 6/2005 | Joffe et al. | |
| 2005/0203349 A1* | 9/2005 | Nanikashvili | 600/300 |

OTHER PUBLICATIONS

Hardesty, Larry, "Clothed in Health," Technology Review, Jul./Aug. 2001, p. 34.

"Micropaq," Wlch Allyn, http://www.monitoring.welchallyn.com/products/wireless/micropaq.asp, retrieved Apr. 16, 2003, 2 pages.

Home Health Telemanagement Service, The University of Illinois at Chicago Medical Center, http://www.uic.edu/hsc/acad/intmed/cardio/monitor/, retrieved Jul. 13, 2005, 1 page.

Boston Medical, http://www.bosmedtech.com/, retrived Oct. 10, 2001, 2 pages.

Kivalo: Wireless Healthcare Informatics, http://www.kivalo.com/, retrieved Oct. 10, 2001, 2 pages.

"Digital Angel: Making Your World a Little Safer . . . ," http://www.digitalangel.net/da/, retrieved Oct. 10, 2001, 7 pages.

Cadionet, http://www.cardionet.com/, retrieved Oct. 10, 2001, 1 page.

The HomMed Central Station, http://www.hommed.com/patients_families/central_station.asp, retrieved Oct. 10, 2001, 1 page.

"BodyMedia Introduces SenseWear Pro Armband Wireless Body Monitoring Device," http://www.thinkmobile.com/news/00/39/23/, retrieved Oct. 10, 2001, 3 pages.

U.S. Appl. No. 10/868,676, Goldberg.

U.S. Appl. No. 10/913,140, Goldberg.

U.S. Appl. No. 11/356,739, Goldberg.

U.S. Appl. No. 10/081,132, Goldberg.

U.S. Appl. No. 10/963,205, Goldberg.

Micropaq(R) Wearable Monitor, Welch Allyn, http:///www.monitoring.welchallyn.com/products/en-us/x-11-ac-100-0000000001100.htm.

* cited by examiner

PERSONAL HEALTH MONITORING AND/OR COMMUNICATION SYSTEM

PRIORITY APPLICATIONS

This application is a continuation in part of U.S. patent application Ser. No. 10/868,676, filed Jun. 15, 2004, which is a continuation of U.S. patent application Ser. No. 09/075,097 filed Oct. 11, 2001, issued U.S. Pat. No. 6,840,904, and claims priority to U.S. Provisional Patent Application Ser. No. 60/562,876 filed Apr. 16, 2004, each of which is incorporated herein by reference in its entirety.

RELATED APPLICATIONS

This application is related to the following pending applications, each of which is incorporated herein by reference in its entirety: U.S. Provisional Patent Application No. 60/653,653, filed Feb. 16, 2005, U.S. patent application Ser. No. 10/913,140, filed Aug. 6, 2004, U.S. Provisional Patent Application No. 60/493,904 filed Aug. 7, 2003, U.S. patent application Ser. No. 10/963,205 filed Oct. 11, 2004, and U.S. Provisional Patent Application No. 60/487,471 filed Jul. 15, 2003.

BACKGROUND

Aspects of the present invention generally relate to monitoring, e.g., obtaining, health-related information, such as, medically-related and/or physiologically-related information, of at least one subject, communication and/or storage of such information, e.g., to, in and/or from a device or computer and/or to and/or from a subject and/or a person or persons associated with a subject, such as a health care provider and/or a family member.

SUMMARY

The present invention generally provides devices, systems, and methods for monitoring health related information of subjects, and/or communicating and/or storing such information. The term "subject" is used herein in a broad sense and where appropriate encompasses non-humans as well as humans. A subject may be a "patient," and unless the context indicates otherwise, "subject" and "patient" are used herein interchangeably. For example, embodiments of the invention may monitor health related and other information, such as physiological information, including but not limited to, blood pressure, heart rate, body temperature, weight, EKG, EEG, glucose level (blood sugar), respiratory capacity (PEAK flow), substances and/or chemical presence or level (e.g., drugs, proteins, hormones, compounds, chemicals and things which may be found in a subject's body, blood, body fluids, etc.), therapeutic effect, efficacy, compliance, etc. Although the present invention may be described by way of example in relation to health-related information and in relation to human subjects, it is understood that the present invention is not limited thereto and is generally applicable to other information and non-human subjects.

In accordance with one aspect of the invention, a modular approach to health-related monitoring is provided. In one embodiment of the invention, a monitoring system is provided that includes at least one device or computer which receives health-related information from at least one monitoring device that includes at least one sensor for obtaining health-related information from at least one subject. In one embodiment, at least one computer receives health-related information from a plurality of monitoring devices each having at least one sensor for obtaining health-related information from a subject. In another embodiment, at least one computer receives health-related information from a plurality of monitoring devices from a plurality of subjects. In such embodiments, each monitoring device communicates with a transmission device, preferably wirelessly, which acts as a communication hub or gateway between the respective monitoring device and the at least one computer or other device.

Monitoring devices may be portable and may be easily worn (e.g., on a wrist, belt, etc.) or carried (e.g., in a pocket, pocketbook, etc.). Transmission devices may be stationary, and may be placed in any convenient location in a home, office, play or exercise facility. A monitoring device or devices and their associated transmission device may be located in a same building or sub-part of a building (e.g., a house, a room in a building, an apartment in a building, an office in a building, etc.). In this respect, a subject may move freely about the building and information will be transmitted between a monitoring device and a transmission device. This allows a monitored subject to locate a monitoring device, such as a scale, in one location, e.g., in a particular room or place in a room, and the associated transmission device in another room or place in a room, e.g., convenient to a communications port (telephone jack, Internet terminal, etc.).

One or more monitoring devices, e.g., a set of monitoring devices, and one transmission device may be provided to service one or more subjects in a specific location or family or other relational group. A set of monitoring devices may include a plurality of the same type of monitoring device and/or a plurality of different types of monitoring devices. The term set is meant in a broad sense and encompasses one or more monitoring devices that operate with a transmission device. A plurality of such sets may be provided for use in different locations or by different relational groups. In one embodiment, each transmission device communicates with one or more remote computers. Information of the type described above is provided by one or more monitoring devices (via one or more transmission devices), to a remote computer and the remote computer may provide information of the type described herein to the monitoring device(s). Since a transmission device may service a number of monitoring devices, and only one transmission device associated with a set of monitoring devices need have communication equipment to provide and receive information from a remote computer, while monitoring devices need only have local communication equipment such as RF, Bluetooth, etc., to communicate with a transmission device. In this respect, in one embodiment, the monitoring device includes a communication unit for communicating with a transmission device, preferably wirelessly, and the transmission device includes a plurality of communication units, one for communicating with at least one monitoring device and one for communicating with at least one remote computer.

In one embodiment, the monitoring device includes a user interface. Embodiments of the user interface may include an output device, an input device, or both. The user interface determines substantially if not exclusively the subject's experience with the process of providing information to a remote computer or device and obtaining and/or receiving information from a remote computer or device (and for display of information by the monitoring device).

An output device, e.g., a display device, for a user interface can provide: status information regarding information being obtained or to be obtained by a sensor; instruction for obtaining such sensor information; physiological measurements; news, messages, etc., regarding a wide range of topics including but not limited to a medical or health condition or conditions of a subject being monitored, a drug trial, statistical information in the medical or health field and/or relating to a medical or health condition or conditions of the subject being monitored, etc.; charts and/or predictive values, e.g., in connection with glucose levels, weight, etc.; measurement information, e.g., blood pressure, heart rate, glucose level, etc.; and/or pose questions relating to or in connection with the foregoing and other topics.

An input device for a user interface may be one or more of a keyboard, a keypad, switches, such as press button, touch, or proximity switches, a touch screen, a digitizer, a mouse pad, etc. An input device may be used to select or initiate an action, e.g., sensing by a sensor, a test or measurement, transmitting information from the monitoring device or requesting information be provided to a monitoring device, or conditioning a monitoring device for a task, etc.

A monitoring device that includes at least an output device allows a subject to interact with the monitoring device. For example, instructions presented on the output device may guide a subject through a measurement or test. With an input device, the subject may respond or initiate interactivity by directly providing information or requests to the monitoring device as opposed, e.g., to participating in an activity by which a sensor provides information to the monitoring device.

In one embodiment of the invention, a monitoring device operates in connection with a sensor or sensors related to a specific physiological sign or medical or health condition. For example, different monitoring devices may be concerned with: blood pressure and/or heart rate; EKG; weight; glucose level; compliance, a drug test; one or more items of blood work; etc.

A monitoring device may process information and provide processed information to a subject. For example, a monitoring device operating with a blood pressure sensor may provide blood pressure readings to a subject. A monitoring device may provide information to, and receive information from, another device, such as a remote computer. In an embodiment of the invention, a monitoring device transmits information to and/or receives information from a remote computer via a transmission device. In this embodiment, the transmission device includes a component of the modular approach referred to above and is separate from the monitoring device. The transmission device provides information supplied by a monitoring device to a remote computer, and provides a monitoring device with information supplied by a remote computer.

In some embodiments, a monitoring device communicates with a transmission device wirelessly using any suitable wireless technology, although wired communications may be used. Since a monitoring device includes a user interface, a transmission device with which the monitoring device communicates need not include a user interface. In such an embodiment, the transmission device may operate according to a default protocol or a protocol set selected by or through the monitoring device or a remote device.

Embodiments of the transmission device may provide for wireless or wired communication between the transmission device and a remote computer using a communications or computer network, e.g., cell phone or mobile phone networks, the public telephone system, the Internet, etc., or over the air. In one embodiment, the transmission device establishes a connection with a remote device via a cell phone, pager, public telephone system, and/or other system, with a priority depending upon available resources. For example, where the transmission device is coupled to a cell phone, the default is to establish the connection through the cell phone, e.g., where the cell phone dials a given number, and if no cell phone is coupled to the transmission device, establish the connection through the public telephone system via a wired or wireless link to the public telephone system. The remote computer generally receives and stores the information provided with the monitoring device, such as physiological measurement, messages, responses to queries, etc.

As mentioned above, monitoring devices may be portable and may be adapted to be worn or carried by a subject, e.g., easily worn by a subject or easily carried in a pocketbook, brief case, knapsack, etc. Transmission devices may be portable in the sense that they are easily and conveniently transportable and can be used wherever connections can be established with a monitoring device or devices and a remote computer or other device. Transmission devices are portable in the sense that transmission device can be transported from one place to another and set up to be used at more than one location. A transmission device may also be fixed in the sense that it is not practical or possible to disconnect and reconnect it, transport it and/or make it operational at more than one location.

Regardless of whether a transmission device is portable or not, in one embodiment, the transmission device is configured to operate with a plurality of monitoring devices. In this embodiment, a transmission device may function, e.g., as a base unit in a household, where one or more members of the household each uses one or more monitoring devices. In this embodiment, the transmission device and/or the monitoring devices are configured so different types of monitoring devices and the transmission device communicate. In one embodiment, monitoring devices and/or the transmission are configured so that different household members may use a same monitoring device to provide information to a remote device that is associated with the particular household member using the device.

In one embodiment, monitoring devices perform all or most of the processing required for providing and configuring or formatting information to be transmitted to a remote device, and the transmission device simply establishes a connection to a remote device, receives information from a monitoring device or devices, and transmits the received information after performing transmission tasks such as modulation, A/D, D/A, etc. The transmission device operates in reverse fashion for information received from a remote device that is to be supplied to a monitoring device.

Described in more detail below is an embodiment which includes one or more monitoring devices, each including a user interface, and a transmission device which services the one or more monitoring devices and preferably does not include a user interface. In this embodiment, the user experience revolves around or is limited to interaction with a monitoring device.

In accordance with another aspect of the invention, a method is provided for establishing communication between a monitoring device and a remote computer in accordance with an initial log-in or registration, either with the remote computer or another computer which carries out a registration function, prior to enabling subsequent communications for transferring information between a monitoring device and a remote computer. According to embodiments of this aspect of the invention, a national/international, e.g., toll-free, number is provided for initial communication with a first remote computer. The information needed for establishing the initial communication, e.g., toll-free number, as well as other information, such as a username, and password, is loaded into a monitoring device prior to this first communication, e.g., at the time a monitoring device is provided to a subject, which may be loaded by the provider of the monitoring device, or after the device is provided to a subject who loads information into the monitoring device. Such information may also be downloaded to the monitoring device according to known methods.

Preferably, the monitoring device may only be used once it has been successfully registered. On power-up, registration status is checked. If the device is unregistered, the user must enter, e.g., a five or six digit access code. In one embodiment, the access code may be obtained by making a voice call to a Contact Center (which may use computers and communication devices different from computers and communication devices that receive, transmit, process, etc. health-related information) that provides a unique serial number necessary to initially register with the service. The Contact Center may link the access code to the serial number of the device in the database.

After the access code is entered or downloaded (e.g., following a prompted session), the monitoring device causes the associated transmission device to call initial number and establish connection with the first computer. After suitable authentication between the monitoring device and the first computer, subject-related information is uploaded to the first computer and information is downloaded to the monitoring device, such as the serial number, local access number, username, password, language, date and local time, web address, ports and cellular phone configuration information from the computer. After completion of the registration process, a monitoring device is ready to obtain and transmit health related information to a second remote computer accessed via the local access number.

The registration process thus swaps the initial telephone number with a local access number. In accordance with one embodiment of the invention, a first bank of modems or other communication devices is provided for communication with the first remote computer via the initial number, and a second bank of modems or communication devices is provided for communication with the second remote computer via the local access number. In this embodiment, the first bank of modems is expected to handle significantly less traffic than the second bank of modems. The reason for this is that each monitoring device is expected to make only one call to the first bank of modems for a one-time registration process, whereas each device is expected to subsequently make multiple calls to the second bank of modems to transfer health-related information.

Therefore, embodiments of this aspect of the invention may provide significantly less resources (e.g., modems, processing power, memory, etc.) associated with the first remote computer and first bank of modems than associated with the second remote computer and second bank of modems. In accordance with this embodiment, higher financial resources associated with the first remote computer may be tolerated from a business model viewpoint than with the second remote computer, e.g., a higher per call rate. This embodiment recognizes the value of swapping from a higher per call rate for the initial call to a lower rate call for the multiple calls expected for transfer of health-related information. This embodiment also recognizes the value from a business model viewpoint of separating the initial registration process in terms of physical and financial resources from the reporting and transfer of health-related information. For example, from a business model standpoint, a party may provide a database for health related information and the first remote computer and first bank of modems, while permitting or requiring a customer to provide and operate second remote computer and second bank of modems which may access the first party's database. The first party may then charge the second party a subscription or per use rate for accessing the database. As an incentive, the first party may provide monitoring devices and transmission devices to the customer at no cost or at a below market cost.

The embodiment described above is not dependent upon a transmission device provided separately from a monitoring device, and may be implement using various configurations of monitoring devices and transmission devices with varying integration configurations, e.g., as described herein or with a local computer or fully or partially integrated monitoring and transmission devices. Similarly, the business model described above is applicable to other applications in various fields including health-related and non-health-related.

In an embodiment described below, a remote device comprises a remote computer and a database for storing subject information and other information. The remote computer may not only receive information from and provide information to monitoring devices, but may also provide information to and receive information from health care providers, family members, etc. The computer may provide and/or receive such information over a network, e.g., the Internet.

A remote computer may be involved with the health and medical condition of individual subjects, health and medical conditions in general, and/or drug tests, clinical evaluations, etc. Thus, a remote computer can collect information from individual subjects, and analyze and process such information in the nature of a health-related database for a specific health issue or condition. Information may be provided, e.g., for research, analysis or other purposes stripped of personal information of subjects. Where a monitoring device includes an input device, subjects may enter demographic information and other information that may be included, e.g., with other subject-related information for, e.g., analysis and research purposes.

Subject-related information may also be used by a remote computer for targeted messages, e.g., health related news, alerts, advertising, etc. For example, where a monitoring device supplies blood pressure information, the information may be used to identify the subject as a candidate for a hypertension drug, etc. Similarly, such a subject may be supplied with an alert of extreme high or low temperatures, or ozone content. A monitoring device that supplies respiratory information may be identified as a candidate for an alert of high ozone content, or high air pollution levels, etc.

In one embodiment of the invention, a monitoring system for monitoring physiological parameters of at least one subject is provided that includes a monitoring device and a transmission device. The monitoring device includes at least one physiological sensor for providing physiological parameter data of a subject and a wireless communication unit. The transmission device includes at least one communication unit for communicating with the monitoring device wirelessly and over a communications network with a remote computer. The monitoring device provides the physiological parameter data to the transmission device wirelessly, and the transmission device provides the physiological parameter data to the remote computer.

In another embodiment of the invention, a monitoring system for monitoring physiological parameters of at least one subject is provided that includes a plurality of monitoring devices and a transmission device. The plurality of monitoring devices each include at least one physiological sensor for measuring a physiological parameter of a subject and a wireless communication unit. The transmission device includes a first communication unit for communicating with the monitoring devices wirelessly and a second communications unit for communicating with a remote computer. The monitoring devices communicate a unique identifier with data measured with the monitoring device to the transmission device wirelessly to associate the measured data with a particular monitoring device or a particular user. The transmission device communicates the measured data to the remote computer.

In another embodiment of the invention, a monitoring system for monitoring physiological parameters of at least one subject is provided that includes a monitoring device and a transmission device. The monitoring device includes at least one physiological sensor for measuring a physiological parameter of a subject, a memory that stores at least temporarily messages received from the computer and responses to the messages, a display unit for displaying the messages, and a wireless communication unit. The transmission device includes a first communication unit for communicating with the monitoring device wirelessly and a second communications unit for communicating with a remote computer. The monitoring device wirelessly communicates data measured with the monitoring device and responses to messages to the remote computer through the transmission device. The monitoring device receives messages from the remote computer through the transmission device in a session that includes communicating measured data from the monitoring device to the remote computer, communicating coordinate data for displaying a graphic image of measured data based on the coordinate data from the remote computer to the monitoring device, communicating messages from the remote computer to the monitoring device, and communicating responses to the messages from the monitoring device to the remote computer. For example, the coordinate data may define axes of graphical data, e.g., in a Cartesian coordinate system, a value versus time, or bar or pie graph data, etc.

In one embodiment, the remote computer initiates interactive messaging, such as interactive voice response (IVR) messaging, based on the information received, such as the physiological measurements. Interactive messaging may be triggered in a variety of ways, such as with thresholds for the information received, such as physiological parameter thresholds, timing thresholds, e.g., between readings or any other event, etc. In one embodiment, the computer executes an interactive messaging IVR script that includes a prompt for the recipient to confirm whether or not the recipient is the intended target for the interactive messaging. The IVR script may also include prompts for the recipient to provide additional information regarding the symptoms and activities relevant to the triggering event.

With respect to compliance, the user interface of a monitoring device may be used to provide and receive compliance-related information.

BRIEF DESCRIPTION OF THE DRAWINGS

The figures of the accompanying drawings are meant to be exemplary and not limiting. Like references in the figures are intended to refer to like or corresponding parts. In the drawings.

DETAILED DESCRIPTION

Figure 1:
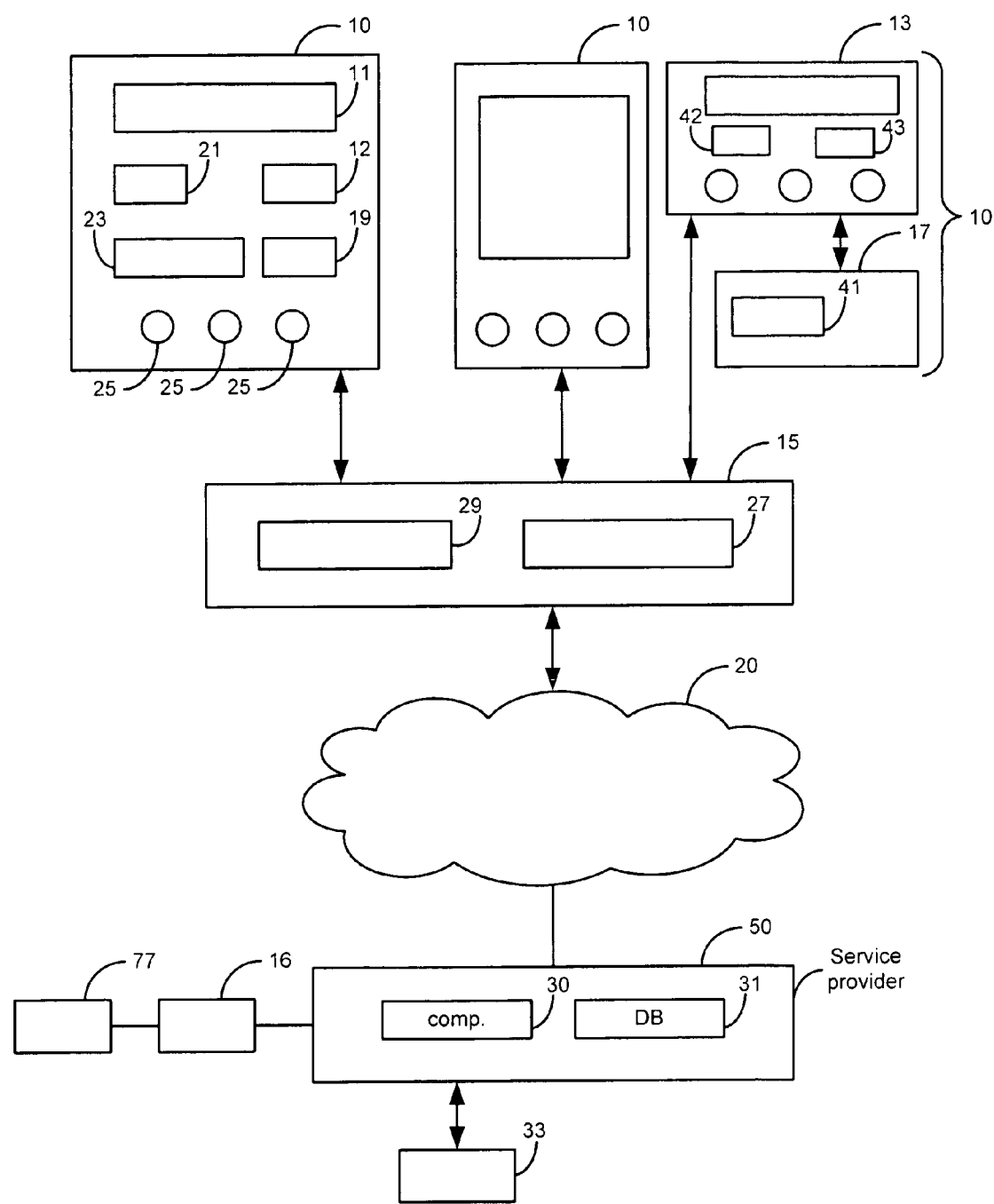
FIG. 1 is a block diagram of a system according to one embodiment of the invention.

Referring to FIG. 1, in one embodiment of the invention, a medical monitoring system is provided that includes at least one computer 30 that communicates with one or more monitoring devices 10, via a transmission device or hub 15, over a communications network 20. Computer 30 is generally one or more server or host computers with access to one or more databases 31 that provide the remote functionality described herein. In one embodiment, computer 30 is not located locally with respect to monitoring devices 10 and may thus be referred to as a remote computer. In one embodiment, the monitoring system includes at least one computer 30 that communicates with a plurality of different types of monitoring devices 10, through the transmission device or hub 15, or otherwise.

A monitoring device 10 may be considered as a data acquisition device for monitoring subjects for health-related information, e.g., physiological or other information. The monitoring device 10 preferably includes at least one sensor 12 for measuring or otherwise sensing directly at least one physiological parameter of a subject. A sensor 12 may be tethered (detachably or permanently) to and communicated with the device 10 by a wire or cable, or the device and the sensor my communicate wirelessly, e.g., using Bluetooth or RF, infrared, sonic or other technology. A monitoring device 10 may include various types of sensors, including, but not limited to, sensors that are used for determining glucose level, weight, blood pressure, body temperature, heart rate, EKG, EEG, substance presence or levels, therapeutic effect, efficacy, compliance, etc. The monitoring devices 10 may therefore be multi-purpose devices, e.g., having a plurality of sensors for measuring different types of physiological parameters, or different types of devices 10 for measuring different types of physiological parameters, such as a weight scale to obtain a user's weight, a blood pressure cuff to obtain a user's blood pressure, a glucose monitor to obtain a user's blood glucose level, etc., or any combinations thereof, such as a combined glucose and blood pressure measurement device. The monitoring device 10 is preferably portable and designed to be wearable by a subject or easily carried.

In one embodiment, the monitoring device 10 includes one or more of the following: an electronic controller 23, an electronic memory 21, a user interface 25 for a user to input information therein, such as buttons or keypad, an output device, such as a display device 11, e.g., a graphic, non-backlighted monochrome liquid crystal display, a communications unit 19, and a power source (not shown), such as batteries. The device 10 preferably includes a clock and/or a calendar or other means for associating a time and/or date with a physiological measurement. The memory 21 generally provides a means for storing information collected with the device or received from the remote computer 30, such as a plurality of measurements, statistical data derived from the measurements, e.g., in chart form or otherwise, user information, e.g., a user identification number, device information, e.g., a serial number, and time and date information. Some or all of the user information may be stored in the monitoring device 10 memory, for example, for later review. The monitoring device 10 is preferably powered by standard batteries or chargeable using a power charger, and may include a battery meter on the display device indicating the power remaining in the monitoring device 10.

For example, a monitoring device 10 may include a sensor 12 in the form of a blood pressure arm cuff which is wired to the device and with, associated parts, is incorporated into the device. In this embodiment, the device 10 includes a display 11 (see, e.g., FIG. 6) that is mounted to the blood pressure cuff. The arm cuff (or other fastener) removably attaches the monitoring device 10, including the display device 11 to a subject. The display device 11 is preferably disposed on the monitoring device 10 at a fixed angle, from about 10 to about 80 degrees, or preferably from about 30 to about 60 degrees from the longitudinal axis of the cuff, to the monitoring device 10 and arm cuff or fastener. The angle of the display device 11 is preferably one that offers easy viewing of the display from the patient's perspective. Thus, the subject need not adjust or otherwise move or tilt the display device 11 to view the display device 11 when the monitoring device 10 is in use.

In one embodiment of the invention, a monitoring device 10 is provided, which includes an electronic controller 23, a display device 11, an electronic memory 21, and one or more sensors 12 for measuring at least one physiological parameter of a subject. A sensor may also detect consumable usage and/or test or otherwise determine at least one physiological parameter of a subject using the consumable. In this respect, the invention beneficially allows an authorized party to determine compliance based on actual usage of a consumable as opposed to indirect or assumed usage based on reporting acts from a subject. For example, actual usage may be assured with a device that determines both usage and blood glucose from a blood glucose sensor.

The monitoring device 10 may also include a communication unit, e.g., incorporated into the device, which communicates information measured or otherwise obtained with the device or any other information stored in the computer memory 21, such as responses to messages, to a transmission device 15. In preferred embodiments, the monitoring device 10 communicates with the transmission device 15 using suitable wireless technology, such as an RF carrier, although other wireless, or wired, communications may be used. In this embodiment, the device 10 includes therein an appropriate transmitter and/or a receiver for communicating with the transmission device 15.

The transmission device 15 generally acts as a hub or base or gateway for one or a plurality of monitoring devices 10, e.g., a plurality of different types of devices, which communicates information received from the monitoring devices 10 to the computer 30. In this respect, the transmission device 15 generally includes a communication unit 27 for communicating with the monitoring devices 10 and a communication unit 29 for communicating with the computer 30. For example, the transmission device 15 may include a transmitter and/or a receiver for communicating wirelessly with one or more monitoring devices 10 and a modem and/or a jack, connector, or other port for connecting to the computer 30 over a network 20, such as a cellular telephone network, the public telephone network, the Internet, or any other network.

As discussed below, the transmission device 15 may be used in combination with a plurality of monitoring devices 10, e.g., used either by a single user or by a group of users in a relational group, such as in a household. In this respect, transmission device 15 and the monitoring devices 10 will generally be located within a certain proximity of each other based on relational use. That is, the monitoring system may be used in a house, apartment, or other residential or commercial unit. In this respect, the transmission device 15 and the monitoring devices 10 may be configured to communicate within a limited distance from each other. This may be accomplished in a variety of ways. For instance, the wireless communication technology used for communication between the monitoring devices 10 and the transmission device 15 may have a limited range, such as by limiting the transmit power for the limited range, operating at frequency that has a limited range as a result of higher attenuation associated with higher frequencies, e.g., 2 GHz vs. 5 GHz vs. IR, etc., or a combination thereof. The plurality of different types of monitoring devices 10 preferably communicate with the transmission using a common protocol thereby allowing a single transmission device 15 to be used as a hub for a number of different types of devices 10.

In one embodiment, a monitoring device 10 is provided that includes a measuring unit 17, such as a scale that includes and/or constitutes the sensor 12, which is remote from, but coupled wirelessly or by wire to, a display unit 13 of the monitoring device 10. For example, a scale can be positioned on a bathroom floor and can communicate a patient's weight or other measured data, e.g., via Bluetooth or other wireless technology, to the display unit 13 of the monitoring device 10. In this embodiment, the measuring unit 17 includes a communication unit 41 for communicating with the display unit 13 of the monitoring device 10, and the display unit 13 includes a communication unit 43 for communicating with the measuring unit 17 and a communication unit 42 for wirelessly communicating with the transmission device 15. The display unit 13 may communicate with the measuring unit 17 and the transmission device 15 with a single communication unit, for example, when using common communication technology.

In one embodiment, the transmission device 15 communicates automatically with the monitoring devices 10 and/or with the computer 30 without any direct prompting from a user. For example, with regard to a monitoring device 10 for monitoring a subject's blood pressure, the monitoring device 10 may automatically signal the transmission device 15 when a physiological measurement has been taken and may automatically communicate necessary information, including the measurement, to the transmission device 15. The monitoring device 10 may also signal the transmission device 15 prior to taking a measurement, e.g., when the device is turned on. In this respect, the transmission device 15 may attempt to connect with the computer 30 while the measurement is being taken to shorten any response time from the computer 30. This aspect of the invention beneficially enhances the user's experience with regard to the real time responsiveness from the system. The monitoring device 10 may also store information therein for later communication, e.g., in the event the monitoring device is not able to communicate with the transmission device 15, and attempt to establish communication with the transmission device 15, as discussed below. The transmission device 15 may then automatically establish communications with the computer 30 and communicate the information received thereto. In this respect, the transmission device 15 does not require a display, however, a signal indicator may be provided, such as an LED or LEDs, which, e.g., flashes to indicate communication is taking place and/or indicate status of the communication. Where transmission device 15 includes a cell phone, which typically includes a display, such display need not be part of the subject experience in the process of communicating between a transmission device and a remote computer or using the monitoring device or sensors.

The transmission device 15 is preferably a portable device, which can be easily transported and can establish a communication connection wherever it is located. In other embodiments of the invention, transmission device 15 is fixed in one location, for example, within a subject's home, such as the households 22, 24 and 26 of FIG. 2. As noted above, the transmission device 15 may also be configured to operate with a plurality of monitoring devices 10, as shown in FIG. 1, whether of different types or otherwise. In this embodiment, the transmission device 15 may be configured to recognize or otherwise identify each of the plurality of monitoring devices 10. This may be accomplished, for instance, by pairing one or more devices 10 with the transmission device 15. Pairing generally entails exchanging passkeys between the monitoring device 10 and the transmission device 15. Once paired, information is communicated only to the intended monitoring devices. This may be accomplished by encrypting communication using the passkeys so that only intended monitoring devices 10 will be authorized to decrypt the information. The devices may also be recognized by a unique device identifier communicated to the transmission device 15 with the physiological or other information. In other embodiments, more than one subject may use the same monitoring device 10. In this embodiment, the monitoring device 10 and/or the transmission device 15 may be configured to associate a particular subject's information with the appropriate person. This may be accomplished by prompting the user of the device 10 to identify himself or herself, in which instance, a unique subject identifier may be communicated to the transmission device 15 with the physiological information. As noted above, the monitoring devices 10 may also include a clock for associating measurements taken therewith with a time and date, which in one embodiment are communicated to the transmission device 15 with the physiological information.

If communication with the transmission device 15 cannot be established immediately, e.g., soon after the physiological measurement has been taken, the monitoring device 10 may attempt to establish communication at a later time. In one embodiment, the monitoring device 10 may attempt several times successively soon after the failed attempt. If communication cannot still be achieved, the monitoring device 10 may store the information and attempt to send the information at a later time, e.g., in 5, 10, 15, 20, etc. minute intervals.

The transmission device 15 generally communicates the information obtained from the monitoring devices 10 to a computer 30 via network 20. The network 20 may be any network or a plurality of networks suitable for communicating information from the transmission device 15 to a remote computer 30, such as a cellular telephone network, or any other wireless network, the public telephone system, the Internet, a local area network (LAN), a wide area network (WAN), an intranet, an extranet, etc. The manner in which the transmission device 15 communicates to the computer 30 will depend on the resources available and a priority assignment where communication can be accomplished via more than one medium. For example, highest priority may be assigned to cell phone communication, followed by communication over the public telephone system. When available, the transmission device 15 may be coupled to attempt to communicate via a cell phone, which provides for maximum flexibility with respect to monitoring subjects away from a particular location, e.g., the subject's residence. If cell phone service is not available, the transmission device 15 may communicate via the public telephone network or over the Internet. The monitoring device 10 and/or the transmission device 15 may also be able to automatically cycle through all possible communication resources to find the one that is available, without user initiation, and transmit the information automatically. This beneficially allows software to more efficiently manage communications regardless of the type of hardware. In one embodiment, monitoring devices 10 are also able to communicate with the remote computer independently from the transmission device 15 and are thus able to bypass the transmission device (if necessary, e.g., when the transmission device is not available) and communicate directly, e.g., via Bluetooth, with a cellular phone that is similarly enabled, e.g., with Bluetooth, a personal computer through a dongle or any other system, or other communications resource. In one embodiment, the transmission device includes a plurality of different types of communications units 29, such as a modem, and/or a communications port such as a USB port, an RS 232 port, a serial or parallel port, through RJ-11 jack/ADSL/cable modem, etc.

Communication of subject information is preferably secure and/or encrypted. For example, patient information can be sent as a single UDP datagram, and error checking can be provided (e.g., checksums, encryption, etc.).

In one embodiment of the invention, at least once, at periodic or non-periodic intervals, or each time the monitoring device 10 communicates with the transmission unit 15 and the computer 30 via network 20, date and time on the monitoring device 10 and/or the transmission unit 15 is synchronized with the date and time of the computer 30.

In accordance with another aspect of the invention, two-way communication is provided to subjects in which information is provided by subjects to a remote computer or person, and information is provided from remote computer or person to subjects. In one embodiment of the invention, such two-way communication is provided via monitoring devices of subjects. In other embodiments, two-way communication is provided via monitoring devices and at least one other device, e.g., a telephone. For example, monitoring devices may provide health-related information to a remote computer as described herein, and based on processing or analysis of such information, a remote computer may provide information for a subject via a monitoring device or a telephone. Telephone communication may be computer controlled, e.g., using IVR technology, or a person may telephone a subject and provide information to a subject. IVR technology is well known and will not be described further herein.

In one embodiment, the computer 30 includes therein software, hardware, or a combination thereof, which establishes or at least attempts to establish communication with the user of the monitoring device 10 based on the information received therefrom. The computer 30, for instance, may initiate communication with the user based on physiological measurements communicated thereto from the monitoring device 10.

For example, the computer 30 may compare incoming data with stored data, such as a value or values or a relationship, such as a threshold, e.g., established based on general standards or for the particular user, or prior statistical data such as average or peak, etc., and initiate communication with the user depending upon the relationship of the incoming data and the stored data, e.g., a value of the incoming data exceeds a stored value. Similarly, an analytic may be run on the incoming data and the results thereof compared to stored data. For instance, if the system determines that the user's weight, blood glucose level, blood pressure, etc., or any statistical derivation thereof, exceeds a threshold for such measurements, the system may attempt to initiate communication with the particular measure accordingly. For example, if the user's blood pressure appears elevated based on stored data for the particular user, the computer 30 may initiate communication with the user to query the user regarding activities and symptoms that may be associated with the elevated reading. Threshold values may be established for a number of other criteria for establishing communication with the user of the device 10. For example, the time between measurements or non-measurement for a period of time may trigger communication.

Various or a plurality of various types of communications may be initiated, including messaging back to the medical device 10, e-mail messaging, facsimile messaging, voice messaging, interactive or otherwise, etc. In one embodiment, the computer 30 attempts to establish communication with the user via an interactive voice response (IVR) system, which prompts users for additional information and/or communicates an appropriate message to the user based on the information received via the monitoring device 10. In this embodiment, the computer 30 communicates via the public telephone network 16 and/or a cellular phone system that provides access to the user with telephonic equipment 77.

In one embodiment of the invention, some or all of the communications between the various devices of the monitoring system are performed in real-time, when possible. For instance, information from the monitoring devices 10 may be communicated automatically to the transmission device 15 once physiological or other information is obtained with the device 10, which may subsequently be communicated automatically to the computer 30. The computer 30 may monitor incoming information and establish or attempt to establish communication with the user once the information is received. In this respect, the monitoring system is capable of real-time monitoring and real-time responses to the monitoring data.

The type of messaging may vary based on the type of data received. For example, the messaging may be words of encouragement for a user participating in a weight management program, statistical information based on the information received, instructions or a warning for, e.g., taking additional measurements or seeking the assistance of a health care professional, prompts for additional information, etc. In one embodiment, the messaging is initiated with an IVR system which executes an appropriate script with a plurality of prompts for additional information, such as the script provided below in Appendix B. The monitoring system is generally applicable to serve a plurality of different users. In this respect, the computer 30 targets the IVR to a particular user, in which instance, the IVR scripts includes at least one confirmation prompt asking the party answering the telephone call to confirm that he or she is the intended target. This may be accomplished simply with a yes or no confirmation, or with a prompt to enter or speak a password or identification number. The IVR script may thereafter include a prompt for addition information regarding symptoms and activities relevant to the information triggering the IVR messaging and/or words of encouragement.

The IVR messaging may be targeted in a variety of ways. For instance, the database may include one or more contact telephone numbers for the monitored subject, such as a home and work telephone number. Preferably, the system attempts to contact the individual at the most likely location. This may be accomplished, for instance, by attempting to contact the subject based on the current time of day or the day of the week. For example, during non-business hours and weekends, the system may attempt to contact the subject at the home telephone number. If successful communication with the particular subject is not established, the system may cycle through the contact numbers available in an effort to contact the individual. More sophisticated measures may also be used to target the individual. For instance, the system may determine the location of the monitoring device 10 and target the contact number associated with the location. The location may be determined, e.g., based on the IP address of the computer used to communicate the information to the computer 30, caller-ID information, GPS data, etc.

In addition to automated messaging, e.g., automatic messaging based on information received, the system may further provide access to the information received and/or messaging capability to authorized users, such as users of the monitoring device 10, health care providers and professionals, partners, caregivers, family members, and any other interested party. In this embodiment, the computer 30 may communicate with a user computer 33, such as a personal computer, personal data assistant (PDA), cell phone, or any other device capable of communicating with a remote computer and capable of displaying at least one graphic user interface for accessing the stored information.

Figure 2:
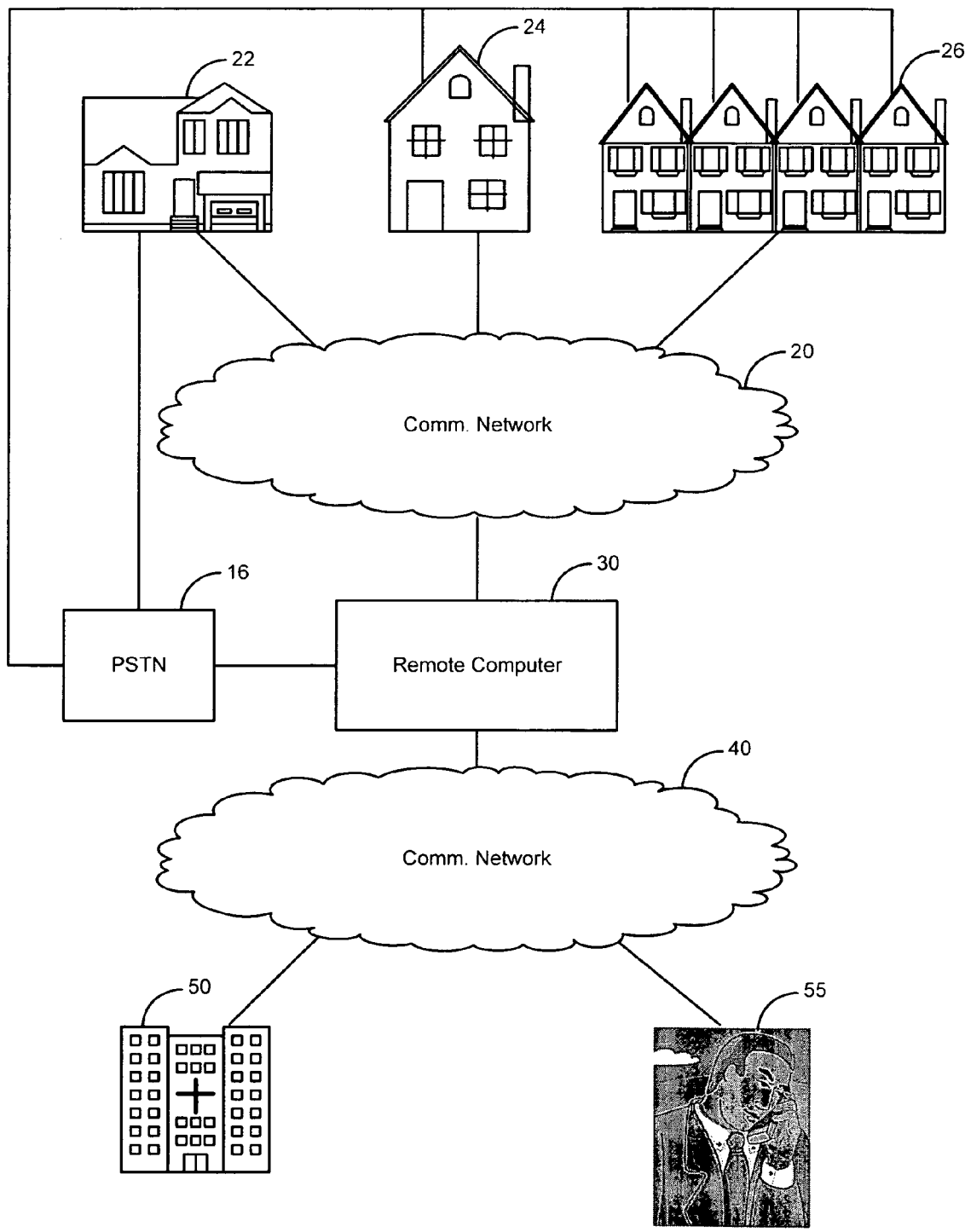
FIG. 2 is a block diagram of a system according to one embodiment of the invention.

Referring to FIG. 2, which depicts households 22, 24 and 26, network 20, computer 30, network 40, service provider 50 and recipient 55. As discussed herein, a monitoring device or a plurality of monitoring devices 10 and a transmission device 15 can be located within a household, such as household 22, 24, and 26 to serve one or more users therein. The term household is used herein in a broad sense to include any location in which a monitoring device 10 and transmission device 15 may be located. The households 22, 24, and 26 are connected to remote computer 30 via a network 20, described herein, which includes for example, a cellular telephone network, the public telephone system, the Internet, etc., or any other network. The computer 30 generally includes a processor, memory storage, and other common computer components suitable to execute the systems and methods described herein. The computer 30 will typically include or access a database 31 to store a monitored subject's information, as well as other information. The database is preferably a relational database. The database may generally include various types of information regarding the particular user that are relevant to the physiological parameter being monitored, such as the user's contact information, physician(s) and their contact information, emergency contacts, medications, allergies, medical history, clinical evaluations, family histories, hospitalizations, medical visits, physiological measurements, e.g., glucose, weight, blood pressure, etc., thresholds, goals, passwords or identification numbers, unique device identifiers e.g., serial number, etc.

Computer 30 may communicate patient information or other information to service providers 50 and one or more recipients 55 via network 40. The network 40 may be a cellular telephone network, the public telephone system, the Internet, etc., or any other network. Service providers 50 may be a doctor, hospital, medical provider, emergency medical services, or another service provider who may provide a service to a subject user based on subject-related information, such as the information entered into or measured with the monitoring device 10. Recipient 55 may be a family member, interested individual, or any other person who may wish to receive the monitored subject's information.

As noted above, the computer 30, service provider 50 and recipient 55 may also communicate with the monitoring device 10 via the network 40, computer 30, network 20, and transmission unit 15, for example to supply information or questions in response to received patient information. An "envelope" icon or other message indicator may appear on the monitoring device 10 display, or an audible message indicator alert may sound when such information is received from a service provider 50, recipient 55 or the computer 30. A message from the computer 30, service provider 50 and recipient 55 may require an acknowledgement from the user, for example, before a user can take a measurement or use the monitoring device 10, the user will be required to read a message and respond to it or otherwise acknowledge the message. The response or acknowledgement entered into the monitoring device 10 is communicated over the network 20 to the computer 30, service provider 50 or recipient 55.

When a user first obtains a monitoring device 10, the user, in one embodiment, must register the monitoring device 10. For example, a user may enter an access code into the monitoring device 10 to "unlock" the monitoring device 10 to allow it to register with the system. Informed consent information, such as system terms and conditions, may also be displayed to a user and acknowledgement or acceptance required prior to initiating a monitoring device 10. In a first communication between the monitoring device 10, transmission unit 15 and computer 30, a connection may be established through a toll free number to register the user with the system and to download a local dial in number for future use. The access code may be a unique access code that may be stored with the device 10 to identify the particular device and/or the user, or some other unique identifier, such as a serial number, may be stored with the device to identify the device, the user, or a combination thereof.

Figure 6:
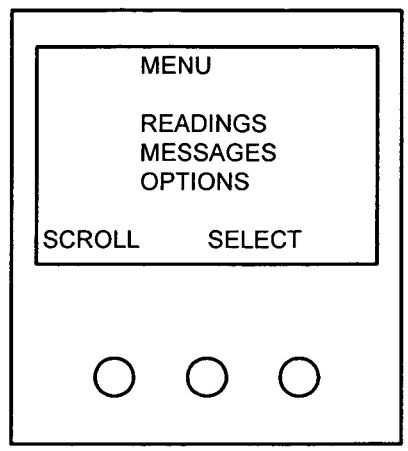
FIG. 6 is a view of a monitoring device that depicts a display for the monitoring device showing a main menu interface screen according to one embodiment of the invention.

After a user has registered or otherwise logged into the system using the monitoring device 10, a menu may be displayed on the display listing the primary information associated with the daily operations of the monitoring device 10, as shown in FIG. 6, which depicts a display for a blood pressure monitor. The first menu may include a readings selection menu item for accessing physiological information obtained with the device 10, a messages selection menu item for accessing messages communicated to the device 10, and an options selection menu item for specifying device options. Device 10 may also display button identifiers or labels that identify the function of the buttons of the device, e.g., a scroll identifier, a select identified, etc. A user may select a menu item to go to a next screen that is displayed in response to the selection.

Figure 7:
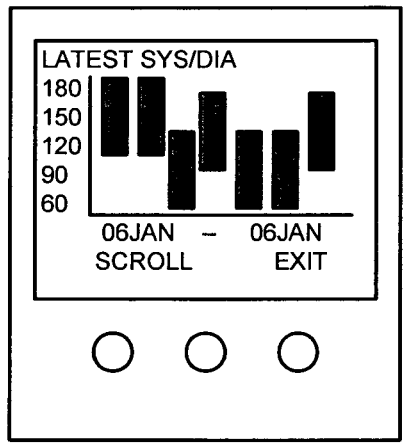
FIG. 7 is a view of a monitoring device that depicts a display for the monitoring device showing readings taken therewith in a graphical display according to one embodiment of the invention.

Upon selection of the readings menu item, the device may display a measurements screen that includes measurements obtained with the device 10. Measurements may be shown on the monitoring device 10 display in more than one way, such as numeric data or graphical data, or a combination thereof, as shown in FIG. 7. Measurements are preferably shown in the order of the measurement, e.g., by time, day, week, month, etc. The device preferably provides scroll functionality to display readings for other days. The graphical representations of the measurements may be determined locally, e.g., on the monitoring device, or remotely, e.g., by the computer 30, in which instance, the computer may communicate coordinate data, as well as other graphical data, for displaying the graphical image of the measured data or derivations thereof, e.g., statistical derivations, on the display of the monitoring device 10.

Figure 8:
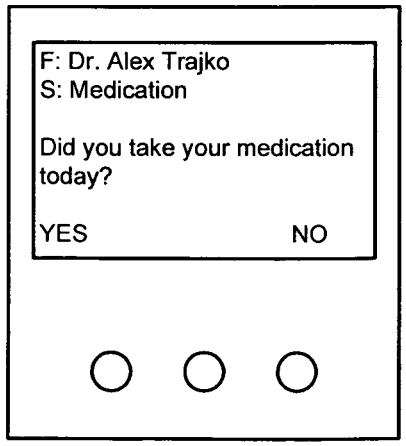
FIG. 8 is a view of a monitoring device that depicts a display for the monitoring device showing a message that prompts the user for additional information in a short messaging format according to one embodiment of the invention.
Figure 9:
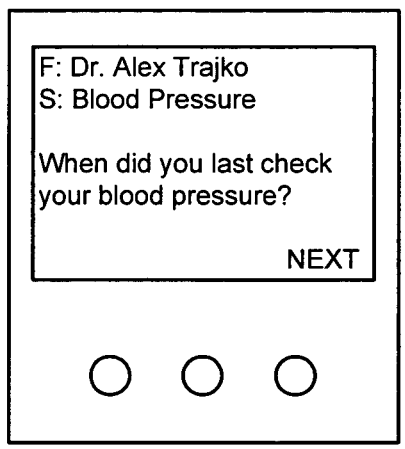
FIGS. 9 and 10 is a view of a monitoring device that depicts a display for the monitoring device showing a message that prompts the user for additional information in a long messaging format according to one embodiment of the invention.
Figure 10:
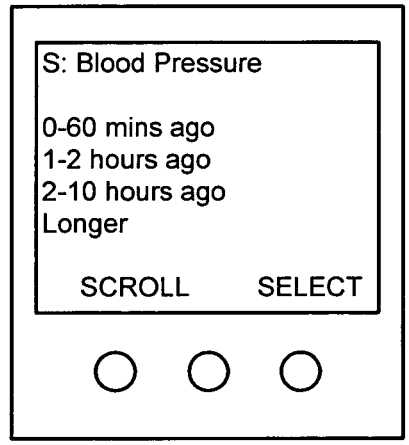

Upon selection of the messages menu item, an appropriate messaging screen is displayed. The messaging screen may provide a list of opened and unopened messages, which may be selected by the user for viewing. Upon selection, the contents of the selected messages are displayed. As noted above, messaging may vary. The messaging may be a prompt for information, such as a compliance query, as shown in FIG. 8, which shows a message from, e.g., computer 30, a service provider 50, or recipient 55, inquiring whether the user has taken medication. Similarly, the messages may inquire regarding use of the device, as shown in FIG. 9 and FIG. 10, which may serve as a gentle reminder for the user to use the device more often.

The monitoring device 10 options can be changed by selecting an option selection on the display menu, which may provide access for changing configurable features, such as alerts, beeper, signal, connection, or transmission features. Connection settings generally permit a user to set connection preferences, such as dial up number, dialing pattern, line access, etc. As mentioned, the user experience is with the monitoring device 10 so that such settings are made via the monitoring device rather than the transmission device 15. Alternatively, or in addition, the transmission device 15 automatically determines the type of connection being used. Transmission settings also allow a user to set transmission, e.g., enable or disable, for example when a user is in a hospital and transmission must be turned off.

Figure 11:
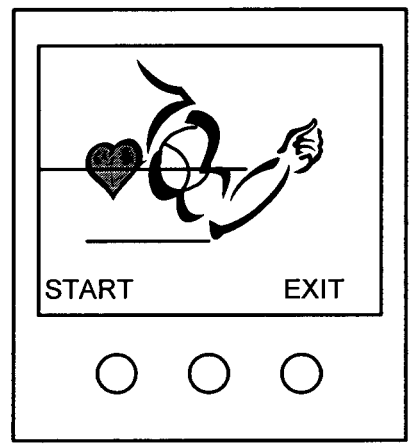
FIG. 11 is a view of a monitoring device that depicts a display for the monitoring device showing direct the user with regard to proper use of the monitoring device according to one embodiment of the invention.

To initiate a measurement, a user may select a start button on the device. Selecting the start button can cause a graphical representation that instructs the user of the proper placement and/or use of the monitoring device 10 screen, as shown in FIG. 11. With regard to a blood pressure cuff, the correct placement of the monitoring device 10 is depicted to assist the user in obtaining a correct blood pressure measurement.

When a user is ready to take the measurement, the user may initiate a measurement through an input to the monitoring device 10. When the measurement is completed, the reading will generally be displayed on the screen of monitoring device 10 and stored to memory at least temporarily with the time and date the measurement was taken. If there was an error in the measurement, an error message may be displayed on the screen, and the user may be prompted to repeat the measurement.

In one embodiment of the invention, a communication session is initiated and the subject's information is communicated from the monitoring device 10 to the computer 30 via network 20 at about the time the measurement is taken. Data is transmitted by the transmission device 15 as described above. The monitoring device 10 screen can include indications that the subject's information is being transmitted, such as a transmission or connection icon. When the computer 30 has been reached, confirmation that the information has been received by the computer 30 may also be indicated by the monitoring device, e.g., with a display on the monitoring device 10 screen, or an audible signal. If computer 30 cannot be reached, an indication of the failed communication will be indicated on the monitoring device screen.

The monitoring device may include a plurality of buttons that are used in conjunction with the display to provide the monitoring device 10 user interface. For example, a left and a right button may be included that are context dependent soft keys, that is, their function depends on the current state of the system operation. A center button may be used for a Start/Escape key. From the main menu screen, the center button may be used to start a measurement. From any other screen, the center button may act to exit the current screen and return the user to the main screen. The soft keys may also be remotely programmable. That is, a message communicated to the monitoring device may include a label for one or more soft keys that represent a response to the message. The user may then respond to messages by selecting the desired key.

Figure 3:
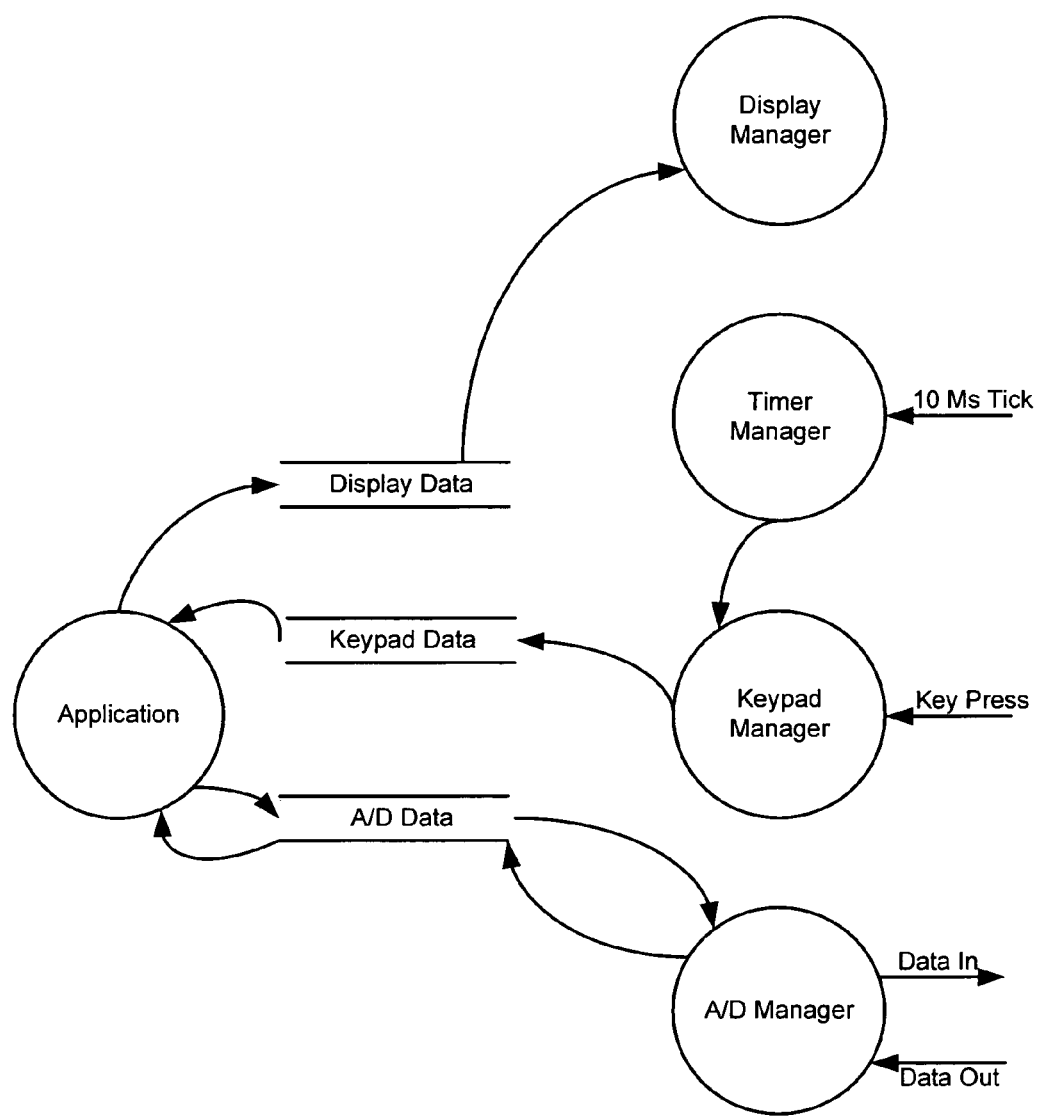
FIG. 3 is a flow diagram of device drivers according to one embodiment of the invention.

The monitoring device 10 may include several device drivers, as shown in FIG. 3, such as a Timer Manager that maintains, e.g., a 10 millisecond, time base to provide system wide timing for the polling of keys or buttons, updating the display and other general purpose timing requirements, a Display Manager that provides a transparent interface to the LCD display, a Keypad Manager that debounces and posts keypad entries to the application software, an Eeprom Manager that provides an interface for non-volatile data storage, a communications Manager that provides access to/from the communication (RF) system, or other device drivers.

The Timer Manager generally uses a timer 0 to generate an interrupt, e.g., every ten milliseconds. The timer manager maintains a timer for each of the following: Keypad Poll Timer, e.g., of 20 milliseconds, which when the time expires activates the keypad manager so that it can poll, debounce, and post any keys that have been pressed, a Beeper Timer, which allows a single-tone beeper to be activated with a variable duration On/Off time, and General Timers, which are used by the application to send callback messages to itself at defined intervals.

Figure 4:
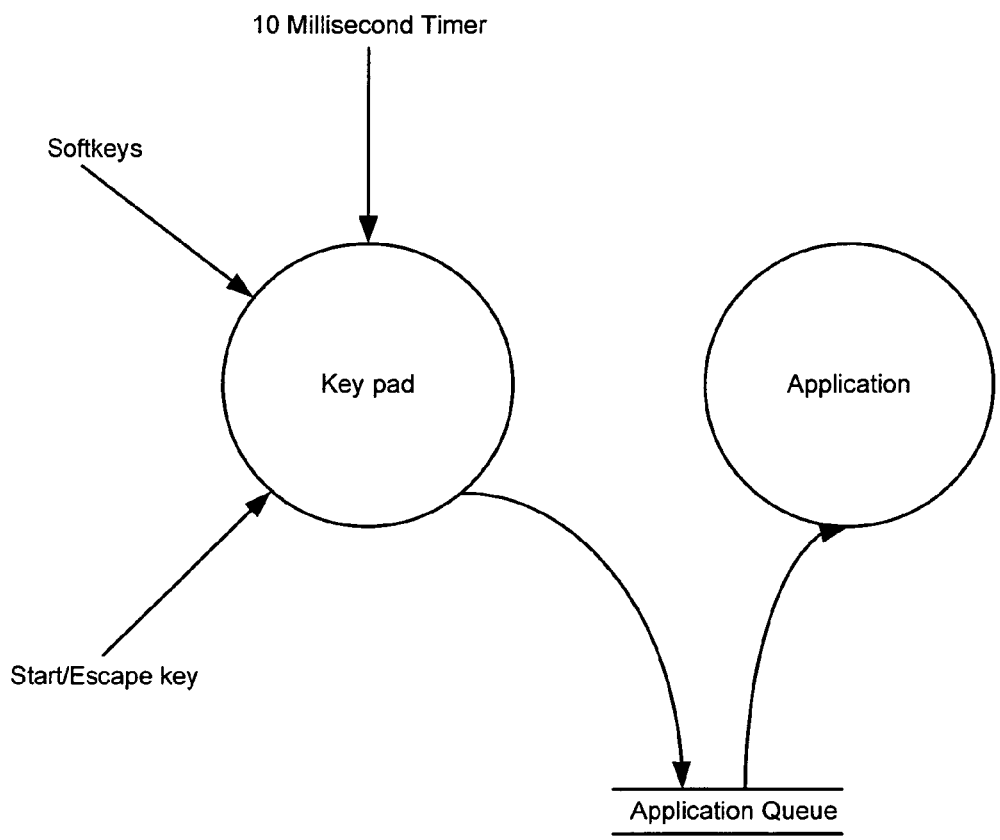
FIG. 4 is a flow diagram of key process according to one embodiment of the invention.
Figure 5:
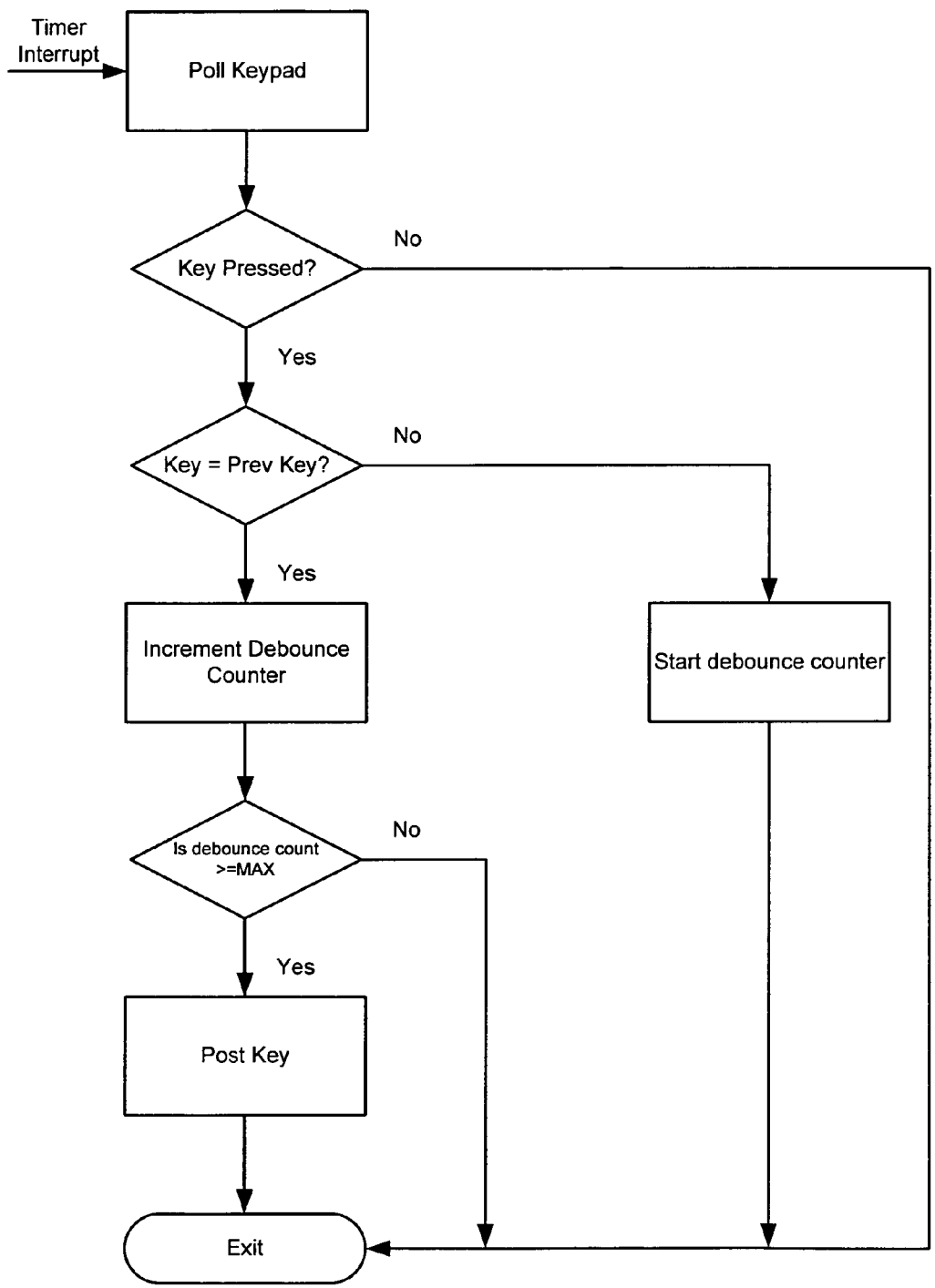
FIG. 5 is a flow diagram of key flow according to an embodiment of the invention.

The Display Manager performs initialization of the monitoring device 10 display controller and accepts text strings (Null terminated character arrays) from the application for display on the monitoring device 10. The API calls may include:

InitDisplay( );
This initializes the display controller.
ClearDisplay( );
This clears the display of any data.
DisplayString(char *string, byte_t position, byte_t mode)
This displays a text string at the starting at the desired character position.
The modes are: Normal, Inverse, Underscore The Keypad Manager may be invoked by the timer manager at a rate of 20 milliseconds. The manager maintains a state machine to debounce and process key presses. Multiples of the 20 millisecond rate are used to move a key or button through the state machine. The states of the state machine may include: New Key—Key initially pressed, Waiting For Debounce—Key is held, Debounced—Key was held for required time. When a key reaches the Debounced state, it is posted to the application. The keypad process is depicted in FIG. 4 and the keypad flow diagram is depicted in FIG. 5.

The monitoring device 10 memory can be, for example a 25LC640, 64K bit Serial Electrically Erasable PROM [EEPROM]. The memory is accessed via a Serial Peripheral Interface (SPI) compatible serial bus. The bus signals required may be a clock input (SCK) plus separate data in (SI) and data out (SO) lines. Access to the device may be controlled through a Chip Select (CS) input. Data stored in the Memory can include, for example: system database, multiple measurements, chart data, messages from system, user identification, serial number, time data for the measurements, etc.

The monitoring device 10 may include a built-in A/D converter that is used to measure the battery voltage. The state of the battery is displayed as an icon on the LCD. Three levels: High, medium and low may be represented using these icons.

A measurement of the battery may be taken each time that the monitoring device 10 enters a main menu screen, or, for example at power up.

The transmission device 15 software may be a real time system that is designed as a combination of an interrupt communication system and a polled event handler. The communications sub-system handles RS232 communications (cell phone and modem) as well as radio frequency communications with the blood pressure meter or any other device. The transmission device 15 carries out commands to connect via a network, such as the Internet, cellular telephone, public telephone, to computer 30, and acts as a conduit for communications between the computer 30 and the monitoring device 10.

In one embodiment, the transmission device 15 generally has a modem, such as CMX866 integrated modem chip. The CMX866 is a multi-standard modem for use in telephone based information and telemetry systems. Control of the transmission device 15 is via commands, such as AT commands over a 9600 bps serial interface. The on-chip µController interprets these AT commands and controls an internal DSP, which provides the modem and ancillary functions such as Ring Detection, Call Progress Detection, Hook Switch control and DTMF autodialing.

The transmission device 15 can also have a cellular telephone interface, such as a RS232 serial interface. Hardware flow control using RTS/CTS is implemented. The signal lines available are: Transmit, Receive, RTS (Request to Send), CTS (Clear to Send), and Ground.

The monitoring device 10 and the transmission device 15 (collectively a "client device") may communicate with the computer 30 in a variety of ways. In one embodiment, the client device communicates with the computer using the protocol outlined in Appendix A. The data may be communicated between the devices in a variety of different ways. In one embodiment, the information is communicated to the computer 30 in a datagram or packet that includes at least one actual measurement taken with the monitoring device 10, such as a blood pressure, weight, glucose measurement and the date and time the measurement was taken. Additional information for associating the measurements with a particular user may also communicated to the computer 30, whether in the same datagram or otherwise, such as a unique user identification number, access code, etc., as well as information for identifying the particular type of device being used, such as the serial number, responses to messages, request datagrams, acknowledgement datagrams, etc. Request datagrams generally contain a query or request for action from the receiving device, such as a request to logon, logoff, accept physiological measurements, download charts, messages, etc., from the monitoring device. Acknowledgement datagrams generally contain information that acknowledges a request or completion of a request. For example, an acknowledgement may be communicated from a monitoring device 10 to the computer 30 indicating receipt of a physiological measurement, a message, etc. The acknowledgements may be used, e.g., to track which information items where communicated between devices, such as measurements, charts, messages, etc., to prevent inadvertent multiple transmission of the same information. The various types of requests and acknowledgements are outlined in Appendix A. Various types of information may also be sent to the monitoring device 10 from the computer 30, such as chart data, e.g., coordinates as well as other information for plotting a graphical representation of the measure data, messages (long and short form), request datagrams, acknowledgement datagrams, etc.

As discussed above, computer 30 may include one or more databases which store information of the type described herein, e.g., patient data, health and medical condition data of individual patients, health and medical condition data in general, and/or drug tests, clinical evaluations, data, etc. Computer 30 and/or other computers may access, analyze and process such data in connection with a specific health issue or condition, etc. Information from such a database and other databases may be provided, e.g., for research, analysis or other purposes stripped of user information that may be used to identify particular users, such as the user's name, address, identification number, etc. Where a monitoring device 10 includes an input device or another means for entering information is provided, patients may enter demographic information and other information that may be included, e.g., with other patient information for, e.g., analysis and research purposes. Patient information may also be used in connection with the provision by a remote computer and appropriate databases of targeted messages, e.g., health related news, alerts, advertising, etc. For example, where a monitoring device supplies blood pressure information, the data may be used to identify the patient associated with the monitoring device as a candidate for a hypertension drug, etc. Such a patient may be supplied with an alert of extreme high or low temperatures, or ozone content. A monitoring device that supplies respiratory information may be identified, for example, as a candidate for an alert of high ozone content, or high air pollution levels, etc. The above or another database may be provided for compliance information.

In this respect, the service provider may provide a website or any graphical interface for accessing information, which will generally be referred to herein as a website, for access to such information and/or for messaging particular monitored users. The particular user's information is preferably made available based on specific user entitlement. For instance, a monitored user may be entitled only to information regarding the user's own monitoring, such as the user's own measurements, charts, messages, etc. Similarly, a physician, caregiver, family member, or other interested party will have access only to information particularly entitled to, such as the interested party's own patient(s), family member, etc. In this respect, the monitored user may be provided with an interface or some other means for providing access to his or her information for interested parties. Website users may also be provided with information regarding monitored users without authorization provided the information does not contain any personalized information. For instance, the website users may be provided with statistical data regarding other monitored users, such as average readings for other users with similar conditions, compliance, outcomes, etc. In these respects, website users may first be provided with a logon interface screen prompting the user for a user name and a password.

As noted, a variety of interested parties may be provided access to information based on specific entitlement. For instance, a physician may be provided access to information for the physician's own patients. In this respect, after logging on, the physician will be provided with a list of menu items that provide authorized access to specific types of information, such as personal information regarding all of the physician's patients or subgroups thereof, information regarding the physician's patient's readings or subgroups thereof, messages for the particular physician, an online calendar, etc. The physician may select any one of the monitored users displayed and update the monitored user's information, such as personal information, thresholds for alerts, e.g., IVR, set alerts for the particular person, etc.

The website may also provide an interface for composing messages to be displayed on one or more monitoring devices and displaying messages from the monitoring devices. Messaging may be made available in a variety of ways. For instance, a messaging interface may be provided with a plurality of form elements therewith allowing the user to specify the contents of a message, such as a subject, body, labels for soft keys, priority, recurring or non-recurring, send times, expiration times, etc. In one embodiment, the messaging interface includes a graphic representation of the monitoring device 10, e.g., the display, with the message shown thereon as it would appear on the device. The message may be a short message, which fits on one screen of the monitoring device 10 or a long message, e.g., multiple choice, which spans a plurality of screens of the monitoring device 10. The message may also be composed in a free form or based on a template, which populates the form elements, such as for subject, body, soft-key buttons, etc., based on a predefined template. The messages may also be set-up as alerts that are triggered at certain instances, e.g., exceeding predefined thresholds. Alerts may also be delivered to the monitored user and/or any other interested party using other communication modes, such as e-mail, facsimile, mail, voice messaging (IVR), etc. The website may provide an interface for a user to specify the applicable modes of communication, recipient parties, and/or the content of the alert.

In accordance with another aspect of the invention, a method is provided for establishing communication between a monitoring device and a remote computer in accordance with an initial log-in or registration, either with the remote computer or another computer which carries out a registration function, and subsequent communications for transferring information between a monitoring device and a remote computer. According to embodiments of this aspect of the invention, a national/international, e.g., toll-free, number is provided for initial communication, e.g., via a network of nationwide/international dial-up POPs (points of presence). The information needed for establishing the initial communication, e.g., a toll-free number, as well as other information, such as a username, and password, is loaded into a monitoring device prior to this first communication, e.g., at the time a monitoring device is provided to a subject, which may be loaded by the provider of the monitoring device, or after the device is provided to a subject who loads information into the monitoring device. Such information may also be downloaded to the monitoring device according to known methods.

Preferably, the monitoring device may only be used once it has been successfully registered. On power-up, registration status is checked. If the device is unregistered, the user must enter, e.g., a five or six digit access code. In one embodiment, the access code may be obtained by making a voice call to a Contact Center that provides a unique serial number necessary to initially register with the service. The Contact Center may link the access code to the serial number of the device in the database. As mentioned, the Contact Center may use computers and communication devices different from computers and communication devices that receive, transmit, process, etc. health-related information)

The information collected by the Contact Center may include the full home address of the individual device user, including the postal code, so that a user's local time zone can be determined and stored on the computer. Monitoring devices may not have their unique serial number in read only memory (ROM), instead the serial number may be downloaded from the computer during the initial registration session. To register a monitoring device, a subject may make a voice call to a Contact Center or provide the information via a Contact Center web-site and obtain an access code.

After the access code is entered (e.g., following a prompted session), the monitoring device causes the associated transmission device to call a number, e.g., with a toll-free ISP access number, and establish connection with a computer, and the monitoring device sends a Registration Request datagram to the computer. The computer returns a Registration Datagram to the monitoring device that includes the serial number, local access number, username, password, language, date and local time, web address, ports and cellular phone configuration information from the computer.

Figure 12:
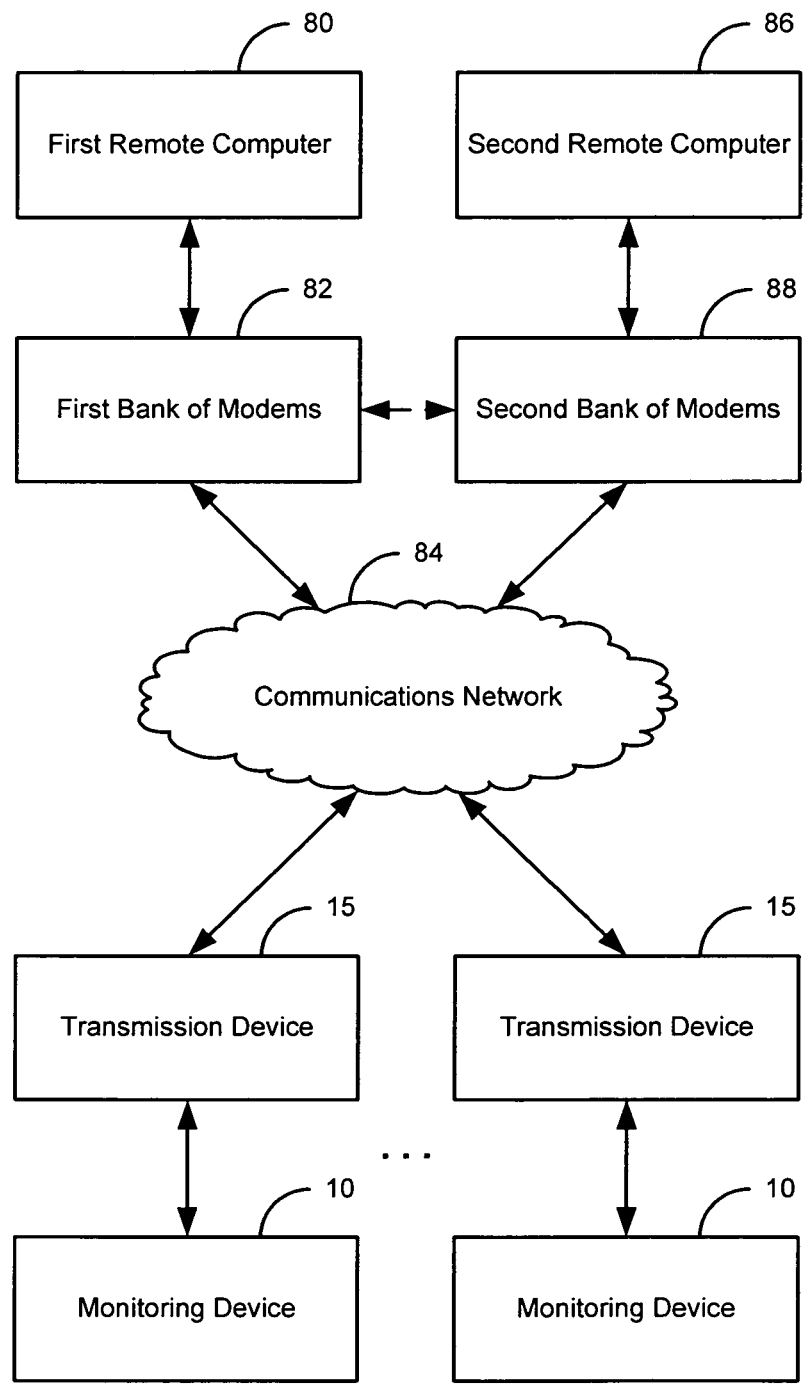
FIG. 12 is a block diagram of a system according to another embodiment of the invention which provides separate resources for registration and transfer of health-related information between monitoring devices and remote computers.

Referring to FIG. 12, after the access code is entered or downloaded (e.g., following a prompted session), a monitoring device 10 causes an associated transmission device 15 to call the initial number and establish connection with a first computer 80 via a communications network 82 (e.g., a cellular phone system or the public telephone system) and a first bank of modems 84 or other communication devices. After suitable authentication between the monitoring device 10 and the first computer 80, subject-related information is uploaded to the first computer 80 and information is downloaded to the monitoring device, such as the serial number, local access number, username, password, language, date and local time, web address, ports and cellular phone configuration information from the computer. After completion of the registration process, the monitoring device 10 is ready to obtain and transmit health related information to a second remote computer 86, a second bank of modems 88 or other communication devices accessed via a communications network (which may be the same or different from network 82) and a local access number.

The first and second remote computers 80, 86 may communicate with each other via respective modem banks and the communications network to transfer, e.g., subject-related and/or registration information, etc.

The registration process thus swaps the initial telephone number with a local access number. In accordance with this embodiment of the invention, referring to FIG. 12, a first bank of modems 82 or other communication devices is provided for communication with the first remote computer 80 via the initial number, and a second bank of modems 88 or communication devices is provided for communication with the second remote computer 86 via the local access number. In this embodiment, as discussed above, the first bank of modems 82 is expected to handle significantly less traffic than the second bank of modems 88. The reason for this is that each monitoring device is expected to make only one call to the first bank of modems for a one-time registration process, whereas each device is expected to subsequently make multiple calls to the second bank of modems to transfer health-related information.

Appendix a Contains Additional Information Relating to Registration and Communication.

While the invention has been described and illustrated in connection with preferred embodiments, many variations and modifications as will be evident to those skilled in the art may be made without departing from the spirit and scope of the invention, and the invention is thus not limited to the precise details of methodology or construction set forth above as such variations and modifications are intended to be included within the scope of the invention.

APPENDIX A

1. Communications between a monitoring device and transmitting device (collectively "client device") and the computer.

A. Client device Internet connection
  I. Client devices may communicate with remote computers using an Internet connection using a PPP (Point-to-Point Protocol) connection to the selected ISP (Internet Service Provider).
  II. The ISP will provide a national/international, e.g., toll-free, number for initial data access, and may also provide an extensive network of nationwide/international dial-up POPs (points of presence). Initial contact may be with a Contact Center (which may use computers and communication devices different from computers and communication devices that receive, transmit, process, etc. health-related information).
  III. The initial, e.g., toll-free number, as well as other information, such as a username, and password, may be loaded into all client devices for registration.
  IV. During registration, a local POP access number (or one that is as close as possible to the user's home address), username, and password may be sent to the client device, for further dial-up communications, unless it is remotely or locally reset.
B. Communication protocol
  I. Communications sessions with the computer may be initiated by the client device requesting either registration or logon to the computer
  II. The client device may first resolve the name of the computer using a DNS (Domain Name System) protocol, and use the IP address of the computer for all further communications for the particular session
  III. The client device and computer may communicate using the UDP (User Datagram Protocol) protocol, and a record may be sent as a single UDP datagram
  IV. Since UDP is a connectionless protocol with no guaranteed delivery, the computer and the client applications may both be responsible for handshaking and monitoring communications timeouts
  V. A communication timeout may occur if there is no valid response from either the computer or the client device for a period of, e.g., 20 seconds or if there is no valid transmission sent or received by either the client device or the computer for a period of, e.g., 120 seconds. A valid response is a response which acknowledges a previous transmission and whose checksum is valid.
  VI. A communication timeout will terminate the session on both the client and the computer, requiring the client device to initiate a new session before data can be transferred.
  VII. At a high level the sequence for datagram communications in a session is as follows:
    a. Registration (a one time session to obtain a soft serial number, a user identification, etc.)
    b. Logon
    c. Send readings from client to computer
    d. Send charts or more generally coordinate data from computer to client
    e. Send messages from computer to client
    f. Send message responses from client to computer
    g. Determine if a triggering event has occurred, if so initiate/conduct an interactive messaging session
    h. Logoff
C. Date and Time Synchronization
  I. The client device clock will be set by the computer at the start of every session, i.e., registration or logon
  II. The computer may synchronize with a time server on the interne to ensure accuracy
  III. The computer may record, e.g., in the database, the home time zone for each client device when it is registered with the Contact Center, or more generally the service provider, based upon the user's home address IV. The computer may convert and transmit all date and time information to the client device from "universal time", e.g., Greenwich Mean Time, to the user's home local time V. The computer may convert and store all date and time information received from the client device from the user's home local time to "universal time"

D. Language Preference

I. The client device and the computer may store the user's language preference

II. The default language may be US English

III. When the client device is first used or after a reset, the user may be asked to enter/confirm their language selection IV. If the user specifies another language, the computer may store the language preference and download the language preference to the client device during registration E. Registration I. Preferably, the client device may only be used once it has been successfully registered. On power-up, registration status is checked. If the device is unregistered, the user must enter, e.g., a five or six digit access code.

II. The access code may be obtained by making a voice call to a Contact Center that provides a unique serial number necessary to initially register with the service. The Contact Center may link the access code to the serial number of the device in the database.

III. The information collected by the Contact Center may include the full home address of the individual device user, including the postal code, so that a user's local time zone can be determined and stored on the computer. The language preference for the user's client device should also be collected and stored by the Contact Center.

IV. Client devices may not have their unique serial number in read only memory (ROM), instead the serial number may be downloaded from the computer during the initial registration session. The serial number may be a unique integer, e.g., whose binary representation fits within 32 binary bits and is 10 decimal digits long, with a significant (non-zero) digit in the first position (i.e. decimal numbers from 1,000,000,000 to 4,294,967,295)

V. To register the device, the customer may
  a. Make a voice call to the Contact Center or provide the information via the Contact Center web-site and obtain an access code
  b. Enter the access code on the device
  c. Connect the device to computer, e.g., with the toll-free ISP access number
  d. The device will send a Registration Request datagram to the computer
  e. Receive a Registration Datagram, with the serial number, local access number, username, password, language, date and local time, web address, ports and cellular phone configuration information from the computer
  f. Send a Registration Acknowledgement record to the computer
  g. If the Registration Status field is not equal to 0, the client device will reset itself to factory default settings and terminate the call, otherwise, the computer will store the status of the device as Registered F. Logon and Logoff I. After successful registration, the client device will be required to logon to the computer to start a communications session II. To logon, the client device may
  a. Connect to sever, e.g., using a local ISP access number
  b. Send a Logon Request record to the computer
  c. Receive a Logon Data record, with the local time, etc.
  d. Send a Logon Acknowledgement record to the computer III. The client device may initiate a normal logoff once all data to be sent from the device has been sent and acknowledged, and no data has been received and validated from the computer for, e.g., 15 seconds. To logoff, the client device
  a. Sends a Logoff Request record to the computer
  b. Receives a Logoff Acknowledgement record from the computer G. Uploading blood pressure monitoring (BPM) Readings I. Once logged on the client device may start sending any readings that have not yet been successfully uploaded to the computer II. One BPM Reading record may be sent in a single UDP datagram from the client device for each reading taken III. Each valid BPM Reading record sent to the computer may be acknowledged by the computer with a BPM Reading Acknowledged record.

IV. If the BPM Reading record is already in the computer database (i.e., the serial number, systolic, diastolic, heart rate, and converted bpm_reading_date all match an existing database record) no duplicate record will be recorded in the database, but the computer may send a BPM Reading Acknowledgement record to the client device.

V. The client device may modify its database when a BPM Reading Acknowledged record is received from the computer to indicate that record should not be uploaded to the computer again H. Downloading Charts I. The client device may send a chart request datagram to start the chart downloading process. This may be done anytime after a successful logon and readings transmission. The computer acknowledges with a chart datagram, which includes the number of charts to be downloaded. The device then accepts one chart page datagram for each chart and acknowledges each one with a chart acknowledged datagram. The process ends when the number of charts expected is received and acknowledged II. By default the computer may download all available (up to 10) chart types unless the user has specified otherwise, e.g., on the Contact Center's web site III. The computer may generate a unique Chart ID for each chart that may be stored on the client device as well for unique identification IV. The chart types may include
  a. Systolic
  b. Diastolic
  c. Systolic & Diastolic
  d. Heart Rate V. The chart frequencies may be
  a. Latest
  b. Daily
  c. Weekly
  d. Monthly VI. To provide a graphical representation, e.g., bars, on the client device, the computer may supply an top left and bottom right absolute screen co-ordinates for each bar.

The areas defined by the two extreme co-ordinates for a bar may be filled in black on the display.

VII. The computer may also transmit the values of the chart labels, such as values for Vertical Label 1 for the top label and Vertical Label 5 for the bottom Label. Similarly, Horizontal Label 1 may be transmitted for the left label and Horizontal Label 2 for the right label.

VIII. The computer may also transmit the exact number of characters to fill each cell, including blanks for positioning properly within the cells.

I. Client Device Messages

I. Users, Professionals, Caregivers, and Partners may use a form on the service provider web-site to enter and send messages to the client devices II. Two types of messages may be available for these users, a short format and a long format. The short format may have fields for From, Subject, 5 lines of text and two button labels for user response, which will generally be displayed on a single screen of the client device. The long format message will have fields for From, Subject, and 5 lines of text for the first screen on the device, and the second screen will show the Subject and, e.g., six, multiple choice answers. For the long format message the button labels may be standardized on the device to permit moving to the next screen and selecting an answer.

III. Once the user starts to review messages, all messages may be required to be reviewed/answered in order unless the escape button is pressed to exit the sequence.

IV. Messages may be flagged as Alerts, and these may cause the device to beep when displayed to the device user until they are answered.

V. The communications process for sending messages to the client device is . . . .
  a. Client sends MessageRequest datagram
  b. Computer responds with Message datagram, which includes a field Number of Messages (left to send)
  c. Client responds with MessageAcknowledged datagram
  d. If message just acknowledged was a long format message, the computer will send a MessageChoices datagram
  e. If a MessageChoices datagram was sent, the client will respond with a MessageChoicesAcknowledged datagram.
  f. Loop until all messages are received or a timeout occurs to end the session.

VI. As the user reviews new messages on the device, the read receipt flag for that message is set in a corresponding MessageResponse record. As the user answers questions posed by the messages, the MessageResponse record stores the response. If a message has its alert flag set, the message may pop up on the device at specified intervals until the user creates an answer. All messages require a user response, even if it is only to indicate they have been read. Message responses may be sent in a later session than the one in which the messages were received or during the same session if so required.

VII. The communications process for sending message responses to the computer is:
  a. The client sends the next unsent MessageResponse datagram to the computer.
  b. The computer sends a MessageResponseAcknowledged datagram to the device. Once received, the device may delete the original message and its response.
  c. Loop until all MessageResponseAcknowledged datagrams have been received or a timeout occurs to end the session.

APPENDIX B

Scenario I: One device, one user, one household, and the user is monitoring his/her blood pressure through a blood pressure monitor that communicates with the computer. Upon receiving a high reading, e.g., exceeding a threshold, the database may trigger an interactive communication call through its IVR system as follows:
  i. "Hello, this is IDEAL LIFE, please press 1 if you are Greg and 2 if you are not"
  ii. Upon pressing 1, the IVR system continues, "we just received your latest blood pressure reading"
  iii. "Please enter 1 if you are feeling dizzy"
  iv. "Please enter 2 if you are feeling tired"
  v. Upon pressing 2, the IVR system continues, "Thank you, good bye"

Scenario II: 2 devices, one user, one household, and the user is monitoring her/his weight and sugar levels through a scale and glucose monitor. The computer may send out, through the IVR system, a triggered interactive communication specifically on the glucose readings even though the user is taking different measurements, as follows:
  i. "Hello, this is IDEAL LIFE, please press 1 if you are Samantha and 2 if you are not"
  ii. Upon pressing 1, the IVR system continues, "we just received your latest weight reading; you are doing great"
  iii. "Please press 1 if you would like to change meal plans"
  iv. "Please press 2 if you would like to change your target weight"
  v. Upon pressing 2, the IVR system continues, "please enter your next target weight loss, enter 1 for 1 pound, 2 for 2 pounds, 3 for 3 pounds, 4 for 4 pounds, 5 for 5 pounds, 6 for 6 pounds, 7 for 7 pounds, 8 for 8 pounds and 9 for 9 pounds"
  vi. Upon pressing 5 the IVR system continues, "now would you like to change your glucose targets? Enter 1 for Yes and 2 for No"
  vii. Upon selecting 2 the IVR system continues, "thank you, and keep up the great work, good-bye"

Scenario III: Multiple users, each with her/his own device, one household, and users are monitoring a specific condition through a specific device. The computer may send out, through the IVR system, a triggered interactive communication specifically based on the right condition of the right individual even though multiple users are in the same household as follows:
  i. "Hello, this is IDEAL LIFE, please press 1 if you are Mary and 2 if you are not"
  ii. Upon pressing 2 the IVR system continues, "Please press 1 if you are John and press 2 if you are not"
  iii. Upon pressing 1 the IVR system continues, "Hello John, we just received your latest glucose reading and would like to ask you a question"
  iv. "If your feet are feeling tingly please select 1, if not select 2"
  v. Upon selecting 2, the IVR system continues, "Thank you John, keep up the great work, good-bye"

Alternatively for Scenario III:
  i. "Hello, this is IDEAL LIFE, this message is form Mary, please press 1 if you are Mary and 2 if you are not"
  ii. Upon pressing 1 the IVR system continues, "Hello Mary, we just received your latest glucose reading and would like to ask you a question"

iv. "If your feet are feeling tingly please select 1, if not select 2"

v. Upon selecting 2, the IVR system continues, "Thank you Mary, keep up the great work, good-bye"

Scenario IV: Multiple users, each with multiple devices, one household, and users are monitoring multiple conditions through multiple devices. The computer sends out, through the IVR system, a triggered interactive communication specifically to the right individual even though multiple users are in the same household and are all monitoring multiple conditions as follows:

i. "Hello, this is IDEAL LIFE, this message is for Sharon, please select 1 if you are Mike, 2 if you are Bob, 3 if you are Sharon"

ii. Upon selecting 3, the IVR system continues, "Hello Sharon, we would like to congratulate you on finishing your weight loss program"

iii. "Would you like to continue monitoring your glucose readings? Enter 1 for YES and 2 for NO"

iv. Upon entering 1, the IVR system continues, "Great, to adjust your levels please select 1, to exit please select 2"

v. Upon entering 2, the IVR system continues, "Thank you Sharon, we will continue monitoring your readings, have a nice day, good-bye."

What is claimed is:

1. A system for use in monitoring physiological parameter data of at least one subject, the system comprising:

a monitoring device which receives physiological parameter data of a subject from at least one physiological sensor and comprises a wireless communication unit having limited range operative to wirelessly communicate over the limited range and a user interface including an input device and a display device, wherein the monitoring device displays at least text on the display device (a) based on input from the input device and (b) based on data received by the wireless communication unit, and the wireless communication unit wirelessly transmits over the limited range first data, including data defining text displayed on the display device and data related to the physiological parameter data, and wirelessly receives over the limited range second data including text to be displayed on the display device; and a local transmission device that communicates with a remote computer over a communications network and communicates over the limited range with the monitoring device, the local transmission device being local to and separate from the monitoring device and being located on a same side of the communications network as the monitoring device, the local transmission device comprising (a) a first wireless communication unit having limited range operative to wirelessly communicate over the limited range with the wireless communication unit of the monitoring device to receive over the limited range the first data from the wireless communication unit of the monitoring device and transmit over the limited range of the first wireless communication unit the second data to the wireless communication unit of the monitoring device and (b) at least one second communication unit that communicates over the communications network with the remote computer to transmit the first data to and receive the second data from the remote computer over the communications network without user operation of a user interface, if any, associated with the local transmission device;

wherein the local transmission device comprises a plurality of second communication units which communicate over the network with the remote computer, one of the second communication units of the local transmission device being initially operable to communicate with the remote computer based on a priority and capability of the respective communication unit to connect to the communications network.

2. The system of claim 1, comprising the at least one physiological sensor which provides physiological parameter dated related to at least one of blood pressure, weight, glucose level, heart rate, and respiratory capacity.

3. The system of claim 1, comprising a plurality of sensors which provide the physiological parameter data to the monitoring device, each sensor for providing a different type of physiological parameter data.

4. The system of claim 1, comprising a plurality of monitoring devices that communicate with the transmission device and at least one sensor for each monitoring device.

5. The system of claim 1, wherein the monitoring device comprises means for associating physiological parameter data received from a sensor with a time and date that the physiological parameter data is received by the monitoring device.

6. The system of claim 1, wherein the monitoring device comprises a memory that stores at least temporarily the physiological parameter data and the display device displays physiological parameter data stored in the memory.

7. The system of claim 1, wherein the monitoring device comprises a memory that stores at least temporarily coordinate data and the display device displays a graphic image of the physiological parameter data based on the coordinate data, wherein the coordinate data is communicated to the monitoring device from the remote computer via the local transmission device.

8. The system of claim 1, wherein the monitoring device comprises a memory that stores at least temporarily statistical data derived from the physiological parameter data and the display device displays statistical data stored in the memory, wherein the statistical data is communicated to the monitoring device from the remote computer and is related to physiological parameter data provided by the monitoring device to the remote computer.

9. The system of claim 1, wherein the monitoring device comprises a blood pressure cuff to which the display device is attached.

10. The system of claim 1, comprising the at least one physiological sensor wirelessly coupled to provide the physiological parameter data to the monitoring device, the at least one sensor being displaceable from the monitoring device.

11. The system of claim 1, wherein the monitoring device communicates a unique identifier with the physiological parameter data to associate the physiological parameter data with a particular monitoring device or a particular subject.

12. The system of claim 1, wherein the monitoring device comprises a memory that stores at least temporarily second data received from the remote computer for display on the display device.

13. The system of claim 12, wherein the second data comprises targeted text messages from the remote computer for display on the display device based on physiological parameter data from the monitoring device provided to the remote computer.

14. The system of claim 13, wherein the targeted text messages comprise at least one of an alert, news, and advertising.

15. The system of claim 12, wherein the monitoring device communicates with the remote computer via the transmission device in a session that comprises:

communication of physiological parameter data from the monitoring device to the remote computer;

communication of coordinate data from the remote computer to the monitoring device related to a graphic image of the physiological parameter data to be displayed on the display device based on the coordinate data;

communication of second data comprising data based on text from the remote computer to the monitoring device; and communication of first data comprising a response to the data based on text from the monitoring device to the remote computer.

16. The system of claim 15, wherein the responses communicated to the remote computer comprise responses to messages communicated to the monitoring device from a previous communication session.

17. The system of claim 15, wherein the session is initiated at about the time the monitoring device receives physiological parameter data.

18. The system of claim 15, wherein the session comprises communication of at least one acknowledgement that indicates receipt of a communication.

19. The system of claim 18, wherein the session comprises a tracking of information communicated between the monitoring device and the remote computer.

20. The system of claim 1, wherein the input device comprises a plurality of switches adapted to be activated by a user, and wherein second data defining at least one message from the remote computer comprises at least one label associatable when the message is displayed on the display device with at least one of the switches, which label represents a response to the message when the associated switch is activated.

* * * * *